US011246674B1

United States Patent
Galbierz et al.

(10) Patent No.: US 11,246,674 B1
(45) Date of Patent: Feb. 15, 2022

(54) ADHESIVE MEDICAL COVER WITH AN INFLATABLE DOME

(71) Applicants: Thomas R. Galbierz, Brentwood, TN (US); Michael A. Galbierz, St. Louis, MO (US)

(72) Inventors: Thomas R. Galbierz, Brentwood, TN (US); Michael A. Galbierz, St. Louis, MO (US)

( * ) Notice: Subject to any disclaimer, the term of this patent is extended or adjusted under 35 U.S.C. 154(b) by 653 days.

(21) Appl. No.: 15/787,673

(22) Filed: Oct. 18, 2017

Related U.S. Application Data

(60) Provisional application No. 62/410,266, filed on Oct. 19, 2016.

(51) Int. Cl.
*A61B 46/20* (2016.01)
*A61B 90/00* (2016.01)
*A61G 10/02* (2006.01)

(52) U.S. Cl.
CPC .............. *A61B 46/20* (2016.02); *A61B 90/06* (2016.02); *A61B 90/36* (2016.02); *A61G 10/02* (2013.01); *A61B 2046/205* (2016.02); *A61B 2090/064* (2016.02)

(58) Field of Classification Search
CPC ...... A61G 10/005; A61G 10/00; A61G 11/11; A61G 10/02; A61G 11/00; A61B 46/10; A61B 46/13; A61B 46/17; A61B 46/20; A61B 46/23; A61B 46/40; A61B 2046/201; A61B 2046/234; A61B 2046/236; A61B 90/36; A61B 90/06; A61B 2090/064; A61M 2025/0253; A61M 25/02; A61M 39/06; A61F 5/12; A61F 5/05816

See application file for complete search history.

(56) References Cited

U.S. PATENT DOCUMENTS

| 2,927,581 | A | * | 3/1960 | Queen | A61F 5/3776 |
| | | | | | 128/873 |
| 3,186,404 | A | * | 6/1965 | Gardner | A61F 5/05816 |
| | | | | | 602/13 |
| 3,874,387 | A | * | 4/1975 | Barbieri | A61M 27/00 |
| | | | | | 602/53 |
| 4,275,719 | A | * | 6/1981 | Mayer | A61B 90/40 |
| | | | | | 128/847 |

(Continued)

FOREIGN PATENT DOCUMENTS

| GB | 2469227 A | * | 6/2010 |
| GB | 2469227 | * | 10/2010 |
| JP | 2011004850 A | | 1/2011 |

*Primary Examiner* — Camtu T Nguyen
(74) *Attorney, Agent, or Firm* — Sandberg Phoenix & von Gontard, P.C.

(57) ABSTRACT

A medical cover is comprised of a stretchable ply which is effectively adhered, at least in part, to the patient during use of the cover. The cover comprises a cover body defining top and bottom edges and first and second side edges, an inflatable zone defined by said body and which is defined by a border, at least one inflation port in the inflatable zone, and at least one instrument access port through which surgical instruments can be passed. The inflation port is connectable to a source of a sterile pressurized lifting fluid or gas, such as air or nitrogen. In use, the medical cover forms a dome which defines an enclosed aseptic zone in which the atmosphere can be controlled.

31 Claims, 14 Drawing Sheets

(56) References Cited

U.S. PATENT DOCUMENTS

| | | | |
|---|---|---|---|
| 4,376,437 A * | 3/1983 | Sundheim | A61M 35/30 602/2 |
| 4,998,538 A * | 3/1991 | Charowsky | A61B 46/10 128/856 |
| 5,538,012 A | 7/1996 | Wiedner et al. | |
| 5,599,289 A | 2/1997 | Castellana | |
| 5,758,660 A * | 6/1998 | Lokken | A61M 25/0111 128/877 |
| 5,803,086 A * | 9/1998 | Scholz | A61B 46/00 128/849 |
| 5,813,409 A * | 9/1998 | Leahy | A61B 17/3423 128/850 |
| 5,979,450 A | 11/1999 | Baker et al. | |
| 5,985,395 A | 11/1999 | Comstock et al. | |
| 6,336,926 B1 * | 1/2002 | Goble | A61B 17/3423 606/34 |
| 7,958,894 B2 * | 6/2011 | Katoh | A61B 42/00 128/849 |
| 8,075,528 B2 | 12/2011 | Widenhouse et al. | |
| 8,137,267 B2 | 3/2012 | Shelton, IV et al. | |
| 8,277,916 B2 | 10/2012 | Cockman et al. | |
| 9,427,255 B2 | 8/2016 | Griffith et al. | |
| 2004/0243073 A1 * | 12/2004 | Lockwood | A61M 1/0092 604/313 |
| 2005/0126577 A1 * | 6/2005 | Griesbach, III | A61B 46/00 128/849 |
| 2006/0251219 A1 * | 11/2006 | Cadwalader | A61B 6/107 378/203 |
| 2006/0293630 A1 * | 12/2006 | Manna | A61B 17/3431 604/327 |
| 2008/0210246 A1 | 9/2008 | Johansson et al. | |
| 2009/0259171 A1 * | 10/2009 | Joshi | A61M 35/30 604/24 |
| 2012/0240942 A1 * | 9/2012 | Llinas | A61B 46/00 128/849 |
| 2012/0255562 A1 | 10/2012 | McGuire, Jr. | |
| 2012/0283626 A1 * | 11/2012 | Belson | A61P 17/02 604/24 |
| 2013/0092177 A1 * | 4/2013 | Chua | A61B 46/10 128/855 |
| 2015/0335322 A1 | 11/2015 | Galbierz et al. | |
| 2016/0074268 A1 * | 3/2016 | Breegi | A61B 90/30 600/21 |

\* cited by examiner

ADHESIVE MEDICAL COVER WITH AN INFLATABLE DOME

CROSS-REFERENCE TO RELATED APPLICATIONS

This application claims priority to U.S. App. No. 62/410,266 filed Oct. 19, 2016, entitled "Adhesive Medical Cover With An Inflatable Dome". This application is also related to App No. PCT/US2017/018171 filed Feb. 16, 2017 (published as WO 2017/143066) and entitled "Medical Drape". Both of said applications are incorporated herein by reference.

STATEMENT REGARDING FEDERALLY SPONSORED RESEARCH OR DEVELOPMENT

Not Applicable.

BACKGROUND OF THE INVENTION

The present invention relates to adhesive medical/surgical covers, and in particular, to an adhesive covering which will form a dome to enclose an area over a site (such as an incision site or a wound) on a patient to maintain an enclosed sterile field around the site on the patient.

Surgery typically involves invasive measures. Opening a wound exposes the patient to ambient atmosphere. Although hospitals and surgery centers have gone to great lengths to eliminate airborne pathogens, doing so is virtually impossible. Surgical site infections (SSIs) thus remain a significant issue, even in hospital-based surgeries. Currently SS's cost the United States' healthcare market billions of dollars annually.

To help reduce the incidence of SSIs, surgical or medical covers/incisable films are typically used to cover the area around the surgical site to maintain a surgical/procedural area on the patient clean and sterile during surgical/medical procedures. Medical covers have been made which are adhered to the patient over substantially the full area of the cover. However, such covers leave the surgical site exposed to the ambient atmosphere of the area in which the procedure is being performed. Thus, even these covers leave a patient subject to getting a surgical site infection.

It would be desirable to provide a system which can form or define an enclosed zone over the incision site to isolate the incision site from ambient air and to maintain a substantially sterile zone over and about the incision site to further reduce the possibility of outside pathogens from entering an incision site and infecting a patient.

SUMMARY

Briefly stated, a dome-forming cover is provided which is intended to be used in surgical applications where a sterile/controlled environment is required. This dome-forming cover can be used as a sterile drape applied to the surgical patient in an aseptic manner. The use of this cover as a drape is intended to reduce surgical site infections (SS's) while improving surgical outcomes and patient satisfaction. It may also reduce costs. The dome-forming cover can be used with both open procedures and laparoscopic (or minimally invasive) procedures.

In accordance with an aspect of the dome-forming cover, the dome-forming cover is formed from a multi-ply film, comprising at least a bottom ply, in the form of a release liner, and a stretchable ply which is adhered, at least in part, to the patient during use of the dome-forming cover. The stretchable ply has adhesive applied to at least a portion of a bottom surface to facilitate adhering of the stretchable ply to the patient. The dome-forming cover further includes at least one inflation port which is connectable to a source of sterile pressurized lifting agent (i.e., a fluid or gas, such as air, $CO_2$ or $N_2$) and at least one instrument access port through which surgical instruments can be passed to manipulate tissues or facilitate manipulation or visualization of tissues within the surgical site. The stretchable ply of the dome-forming cover has a high rate of elongation to allow for expansion when adding a lifting agent between the patient or an incisable film (which can be applied to the patient prior to application of the dome-forming cover) and the stretchable ply of the dome-forming cover.

In accordance with an aspect of the dome-forming cover, adhesives of different strengths can be applied in desired patterns to the bottom surface of the stretchable ply, with stronger adhesives defining perimeter(s) about zone(s) of weaker adhesives to help define the bounds of inflatable zone(s) of the dome forming cover. Alternatively, the dome-forming cover can comprise different thicknesses and/or materials of different stretchability to define the bounds of one or more inflatable zones of a dome-forming cover. In another alternative, the stretchable ply can be heat sealed or otherwise bonded to a lower incisable ply. In yet another alternative, the stretchable ply can have ultraviolet (UV) filtering properties or be composed of a material having UV filtration properties.

The dome-forming cover is applied to the patient over the intended surgical site prior to forming an incision on the patient. Further, the dome over the incision site is formed prior to making an initial incision. This will allow the procedure to be carried out from start to finish in a protected, substantially sterile zone, without exposing the incision site to ambient atmosphere.

In accordance with one aspect of the cover, surgical devices are commonly used in open surgeries, laparoscopic surgeries, or robotic surgeries, and can be inserted through the instrument access port(s) to enable a surgeon (or robot, for robotic surgeries) to perform a surgical procedure on the patient.

In accordance with a further aspect, access ports can allow for tubing or cords to be attached externally of the dome. Access ports can also allow sterile surgical devices to be passed into the dome. These sterile surgical devices may add light, magnify of the wound, manipulate tissue, be prosthetic devices, intra-wound devices and/or closure devices.

Many procedures typically done in open surgical fashion require traction-counter-traction. Hand ports are used to allow surgeons and scrub assistants to manually manipulate tissue, instruments and other devices directly through the dome. Thus, in accordance with another aspect of the cover, the cover can be provided with gloves or hand ports to allow manual manipulation of the tissues or instruments in the surgical site.

In accordance with an aspect of the use of the cover, initially, the surgical site on the patient is prepared and cleaned with a prepping solution, as is common. If desired, a first cover, such as an IOBAN® incisable drape, can be applied to the surface site (i.e., the patient's skin) to further enhance the sterile field around the incision site. This first cover is sized and shaped in accordance with the size and scale to the surgical wound to be created, and will typically be centered over the surgical site. During the procedure, the surgeon will cut (or incise) through this first layer, and the surgeon can thus place the surgical incision at the optimal position.

The dome-forming cover is then adhered to the patient over this first cover and inflated using a flowable agent to form a protective dome or bubble over the incision/puncture site. If the dome-forming cover is heat-sealed to the first cover, then the heat-sealed margins will define the limits of expansion of the dome or bubble.

Insufflation of the dome occurs when pressure from the lifting agent (e.g., $CO_2$ gas) separates the stretchable ply of the dome-forming cover from the first cover (if used) or the patient's skin (if the first cover is not used) and the stretchable ply expands to form a dome over and about the incision site. The expansion of this stretchable ply is controlled typically by an instrument called an insufflator. After desired expansion size determined by the surgical staff, the internal pressure within the dome is kept constant by the insufflator, and the insufflator will add the lifting agent to the interior of the dome as needed to maintain the dome at the desired size.

The instrument access ports can be included with the dome-forming cover, as provided, or can be added to the dome after inflation of the dome. These instrument access ports allow for aseptic access to the interior of the dome. Ports, also known as trocars, have internal valves that allow one-way flow of atmosphere outwardly. In a variation, the stretchable ply which forms the dome can be cured under exposure to light, heat, or other reaction, to become rigid, and to thereby better support instruments which might be received in the ports. In another variation, the stretchable ply can be radiopaque.

The pressure within the dome exceeds the pressure externally of the dome, and this pressure differential inflates the dome, and maintains the dome inflated. It further helps to prevent ingress of contaminating agents into the dome, and thus helps ensure the sterility of the atmosphere within the dome. Because of the positive pressure differential, the dome-forming cover needs to form an air tight seal around the perimeter of the dome. All that is necessary is that the lifting agent be introduced in the dome at a rate exceeding the rate at which the lifting agent may escape the dome.

During a procedure, any tissue removed from the patient preferably will remain within the dome until the procedure is complete, and incisions in the patient have been closed. The dome thus isolates any such tissue and keeps the surgical staff from being exposed to pathogens or potential pathogens from the patient. Any airborne pathogens can be evacuated from the internal dome through gas/air filters, thereby protecting the surgical staff.

Further, the cover can be provided with instrumentation (such as sensors) or other items used during the surgery to be added to the cover before sterilization of the cover (which is typically performed via gamma irradiation). This allows for devices too large to be passed through a port or trocar to be aseptically available within the dome.

In accordance with another aspect of the dome-forming cover, the cover may include additional plies to provide for a secondary or sub-dome formed within a primary dome. Alternatively, in order to supplement the amount of space or room required to perform the surgical procedure under the dome, a second dome can be adhered to the primary dome to effectively increase the size (i.e., height) of the dome. Once the secondary dome-forming cover is affixed to the primary dome, the secondary dome-forming cover is inflated to form the second dome on the primary dome. After insufflation, the base area provided by the secondary dome is removed by cutting and/or opening the primary dome at the base area of the secondary dome to make one continuous dome. This secondary dome must be added to the primary dome in an aseptic fashion.

The dome is inflated prior to incising the patient, and is not removed until incisions have been closed. Thus, the opened surgical site is never exposed to ambient atmosphere. Use of the cover is anticipated to reduce costs related to post-operative care of the patient. Some of the advantages of the dome-forming cover are that:

The dome-forming cover is preferably constructed from films that can be manipulated, constructed and processed by conventional converting methods.

Sterilizing agents can be added to the dome during or after inflation of the dome via ports. Flowable agents can irrigate the wound and then be extracted or evacuated from the wound using irrigation and evacuation devices. Such flowable agents can be a liquid or gas.

The internal atmosphere within the dome can be completely controlled to optimize the surgical outcome. For example, temperature, humidity, pressure, and gas concentrations within the dome all potentially affect the surgical outcome, and thus can be controlled.

The dome-forming cover can be provided with monitoring devices or sensors to monitor desired parameters within the dome, such as atmospheric conditions, such as temperature, humidity, gas concentrations, pressure and the aseptic status, within the dome. Monitoring devices can include an ink (or reactive agent) which changes color in response to a change in the atmosphere within the dome. Physiological conditions of the patient can also be monitored via sensors. The sensors can transmit this information in real time to the operating room staff. Sensor data and actual images of the procedure can be captured during the procedure and utilized for the patient record and be stored as part of the surgical record. This data can be analyzed to optimize patient outcomes and improve surgical technique.

BRIEF DESCRIPTION OF THE SEVERAL VIEWS OF THE DRAWINGS

Corresponding reference numerals will be used throughout the several figures of the drawings.

DETAILED DESCRIPTION OF THE INVENTION

Figure 1:
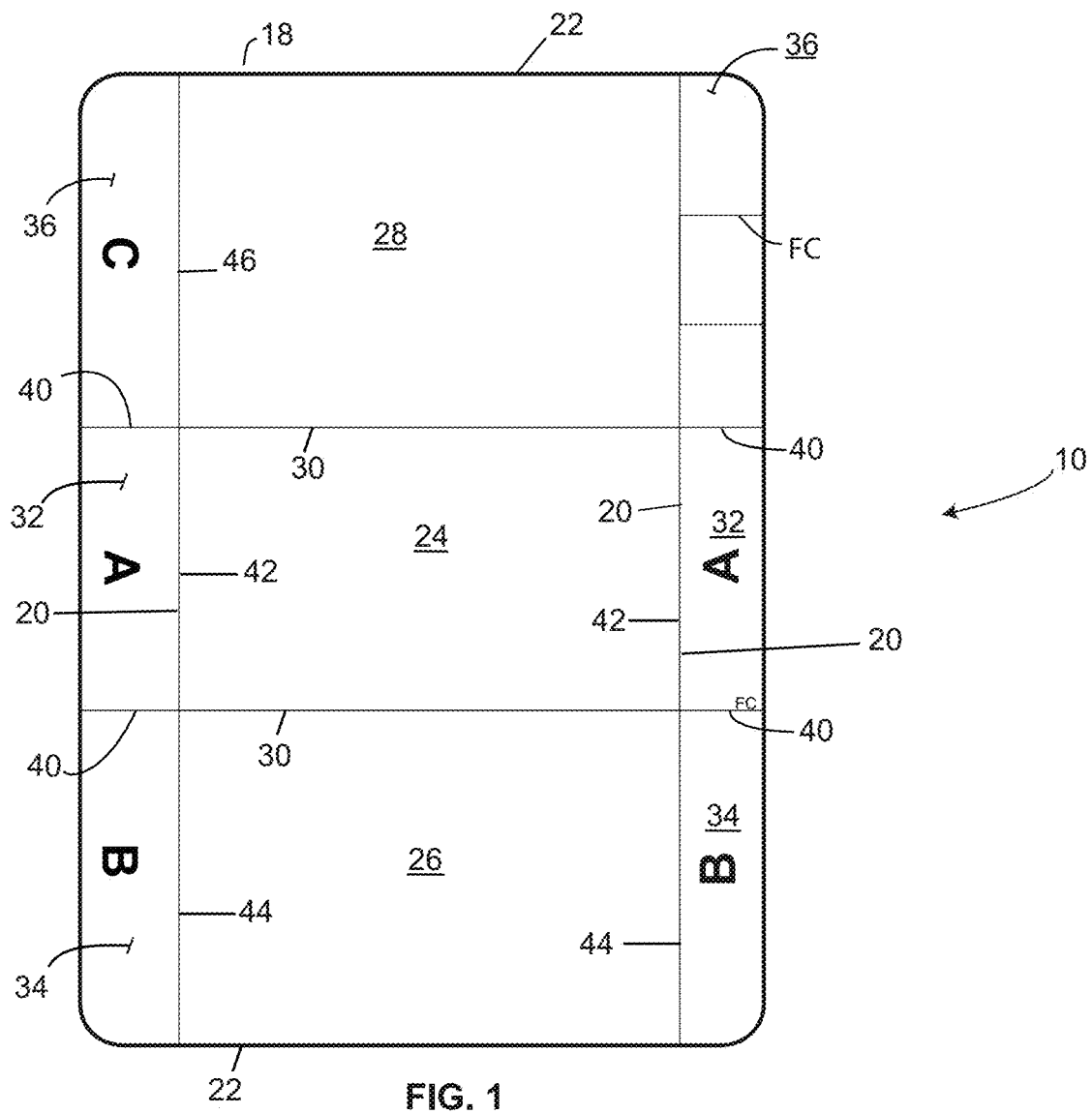
FIG. 1 is a plan view of a dome forming medical/surgical cover.

The following detailed description illustrates the claimed invention by way of example and not by way of limitation. This description will clearly enable one skilled in the art to make and use the claimed invention, and describes several embodiments, adaptations, variations, alternatives and uses of the claimed invention, including what we presently believe is the best mode of carrying out the claimed invention. Additionally, it is to be understood that the claimed invention is not limited in its application to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

Figure 1A:
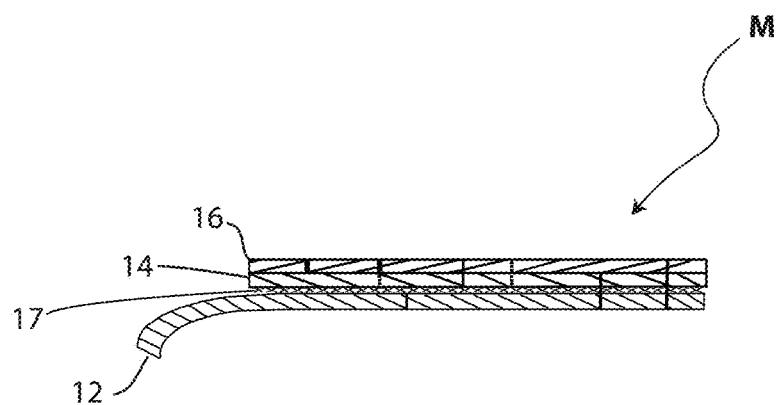
FIG. 1A is a schematic cross-sectional view of the cover demonstrating various cuts/slices through the film from which the cover is formed.

Referring initially to FIGS. 1 and 1A, a dome-forming cover 10 is shown in both plan and in a fragmentary cross-section. The dome-forming cover 10 is made (such as by die-cutting) from a multi-ply material M. The material M can be a 3-ply material comprised of a bottom ply 12, a middle ply 14, and a top ply 16. The bottom ply 12 is preferably a release liner, and can be made, for example, of a substantially non-stretchable material, such as Kraft paper. The middle ply 14 is preferably a polymer film having a substantial amount of stretch in at least one direction; and the top ply 16 is made from a different polymer film which is, at best, only slightly stretchable. As will be described below, at least the middle ply defines a dome-forming ply of the cover. The middle ply 14 has a lower surface coated with a hypoallergenic pressure sensitive adhesive 17 (such as an acrylic or silicone adhesive) to removably secure the bottom ply release liner 12 to the middle ply 14. The adhesive can cover the entire lower surface of the middle ply. Alternatively, the lower surface of the middle ply can have an adhesive free zone which is surrounded by adhesive. If desired, medicaments can be included with the adhesive. The top ply 16 is adhered to the middle ply 14 without the use of an adhesive. For example, the top ply 16 can self-adhere to the middle ply 14 by means of co-adhesion. Although the 3-ply film is a preferred film for the construction of the cover 10, the film used for the cover could just comprise the stretchable ply 14 and the top ply 16, just the bottom ply 12 and the stretchable ply 14, or even just the stretchable ply 14. Further, in desired instances, the adhesive layer 17 can be omitted (to be replaced, for example, with a double-sided tape which would form a border on the cover).

The middle ply 14 and top ply 16 can have desired properties. For example, either ply can have UV filtering properties. The middle ply 14 can be curable under exposure to light, heat, or other reaction, to become rigid. The middle ply 14 can be radiopaque.

A preferred material for the cover 10 when formed from a 3-ply film is 3M 9836 medical tape or film (available from 3M). In this tape, the bottom ply 12 is comprised of a non-stretchable silicone coated paper, which is, for example, about 5 mil (about 0.127 mm) thick. The middle ply 14 is an inciseable polyethylene film or the like, and has an acrylic adhesive 17 applied to a bottom side thereof, to removably secure the middle ply 14 to the bottom ply 12. The middle ply 14 is highly conformable and stretchable, having a high percentage of elongation/stretchability. For example, the middle ply can have an elongation factor of about 300% to about 500%, but the elongation factor can be smaller or greater as desired. Although the middle ply 14 can be breathable, as discussed below, for purposes of the desired application, the middle ply in the preferred film is not breathable (i.e., is air-impermeable). The middle ply can have a thickness of about 1 mil (about 0.03 mm). The top ply 16 can be a polyolefin film with a thickness of about 2.5 mil (about 0.06 mm). The top ply can be slightly stretchable. For example, the top ply can have an elongation of less than about 10%. As such, the top ply is substantially non-stretchable. The top ply is liquid impermeable, and can be either air impermeable or air permeable. The overall cover (paper liner, middle ply, and top ply) has a thickness of about 7.5 mil (about 0.2 mm). When the paper liner ply 12 is still adhered to the middle ply 14, the cover is substantially not stretchable.

The dome-forming cover 10, as noted, can be formed by die-cutting, and thus the dome-forming cover, in an as-supplied form, includes (1) top cuts TC which extend only through the top ply 16; (2) top-middle cuts TMC which extend through the top and middle plies 16 and 14, but which do not extend through the bottom ply 12; (3) full cuts FC which extend through all the plies; (4) bottom cuts BC which extend only through the bottom ply 12; and (5) bottom/middle cuts BMC which extend through the bottom and middle plies 12 and 14, but do not extend through the top ply 16. In addition, and for purposes set forth below, the cuts or slices can be formed as perforated cuts, rather than continuous cuts. Unless otherwise noted, the cuts are continuous cuts (rather than perforated cuts).

The cover 10 (FIG. 1) comprises a body 18 having elongated side edges 20 and top and bottom edges 22. The body 18 is illustratively shown as being divided into three sections, a middle section 24, a first end section 26 and a second end section 28, by back cuts 30 which extend generally perpendicularly between the side edges 20 of the body 18. The cover 10 is shown divided into approximately equal thirds, however, the sizes of the three sections could be altered, if desired. Further, the cover 10 could be made with only two sections or just one section, if desired.

Tabs 32, 34, and 36 extend from the side edges 20 of the cover body 18. As seen, the tabs, in combination, extend the full length of the body sides edges 20. The tabs are separated from each other by full cuts 40 which are co-linear with the back cuts 30, and extend the width of the tabs. The tabs are separated from the body 18 by cuts which extend at least through the top ply of the tape. As shown, tabs extend from both sides of the cover body. However, the cover could be provided with tabs extending from only one side of the body. The cover can be, for example, the cover disclosed in our PCT App. Pub No. WO 2017/143066. The description and operation of the cover, as disclosed in our just-noted application is incorporated herein by reference. In particular, and as described in our just-noted application, some of the tabs are operable to remove the bottom ply 12 (release layer) from the cover to expose the adhesive layer 17, thereby enabling the cover to be adhered to a patent. Other tabs are operable to remove the top ply 16 from the middle ply 14 after application of the cover to a patient, such that substantially only the middle ply remains on the patient.

Figure 2A:
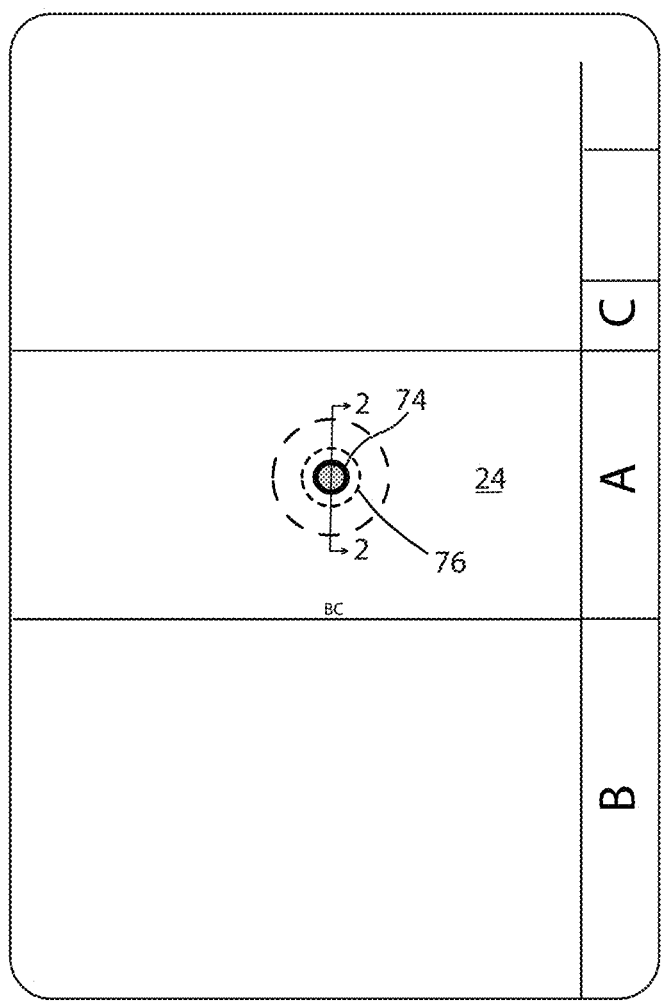
FIG. 2A is a plan view of a cover provided with an instrument access port.
Figure 2B:
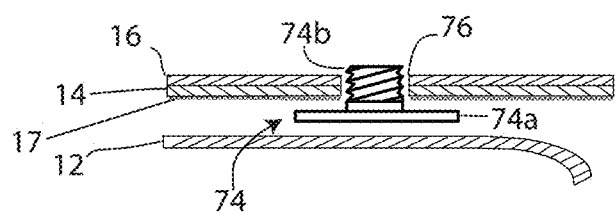
FIG. 2B is a schematic cross-sectional view of the cover with the instrument access port taken along line 2-2 of FIG. 2A.

FIGS. 2A and 2B show the cover 10 with an instrument access port assembly 74 in the middle section 24 of the cover to facilitate use of a scope or instrument with the cover. Illustratively, FIG. 2A shows the cover with tabs extending along only one side of the cover. Instrument access ports can be added to the cover, as described below, to allow access to free space under the cover created by inflation of a portion of the cover using a gas and/or stretching of the middle ply after application of the cover to a patient. These ports can be multi-design/multi-function and include instrument and scopes, as well as mechanical and/or manual access ports, i.e., glove-port.

As shown in FIG. 2B, the instrument access port assembly 74 comprises a base 74a and a hollow neck 74b which extends up from the base. The neck 74b is shown to be externally threaded. The neck 74b could, alternatively, be internally threaded, or could be smooth (i.e., without threads). The port assembly 74 can be designed with or without a valve assembly to allow for passage of a scope or instrument through the neck 74b. An access hole or access aperture 76 is formed in the middle and top plies 14 and 16, respectively, of the cover sized to pass the port assembly neck 74b therethrough. The port assembly base 74a is adjacent the underside of the middle ply in alignment with the access aperture and adhered in place by the adhesive of the middle ply. In the as-supplied condition, the bottom ply 12 will cover the bottom surface of the port assembly base 74a. In the instance wherein cover is made using a two-ply film (which will form the middle and top plies of the cover), the instrument port assembly 74 is adhered to the two-ply film, and then the release liner (bottom ply) is adhered to the two-ply film during manufacture of the overall cover.

Figure 2C:
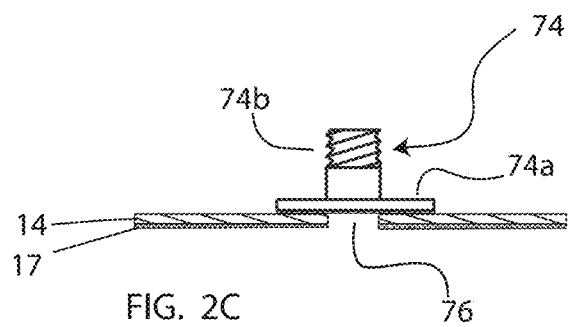
FIG. 2C is a cross-sectional view of a cover with an instrument access port, but wherein the port is applied to a top surface, rather than a bottom surface, of the dome-forming cover.

FIGS. 2A and 2B show a cover in which the port assembly 74 is preassembled with the cover, with the top surface of the cover base 74a adhered to the adhesive ply 17 of the cover 10 (i.e., with the cover base on the bottom surface of the cover ply 14). In FIG. 2C, the instrument access port 74 is shown as being applied to the top or upper surface of the cover ply 14.

Figure 2D:
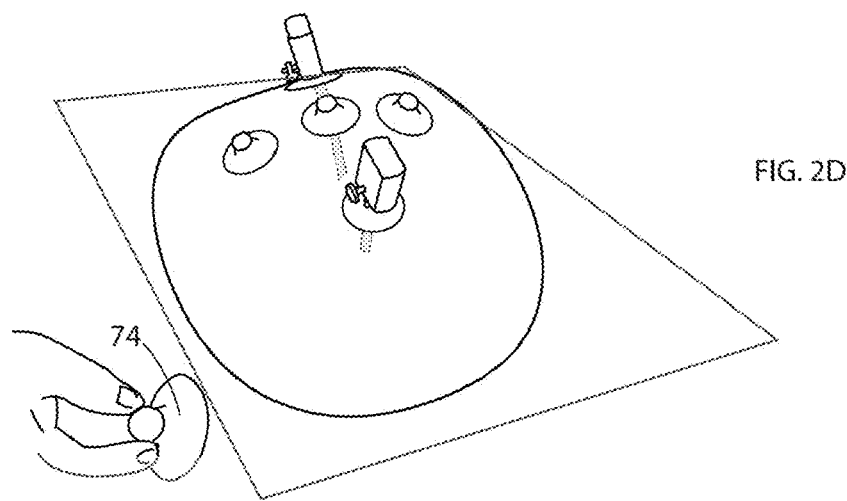
FIGS. 2D-F show an instrument access port being added to an already inflated cover.
Figure 2E:
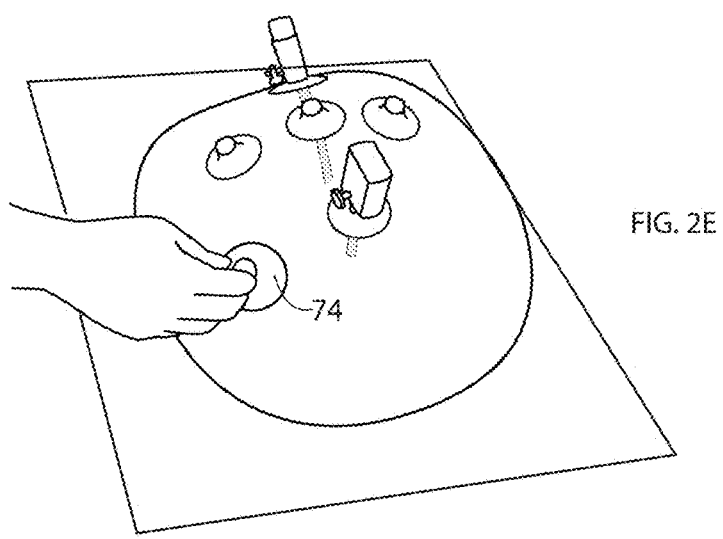
Figure 2F:
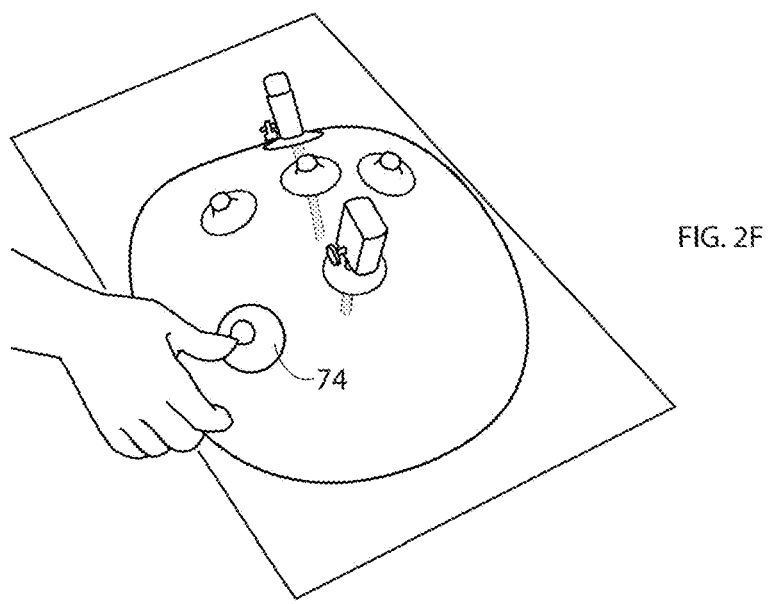

In FIG. 2C, the access aperture 76 in the cover plies/films 14 and 16 is aligned with the neck 74b of the instrument access port. Applying the instrument access port 74 to the top surface of the dome-forming cover, rather than to a bottom surface, allows for the instrument access port to be applied to the cover by the surgical staff at any desired point on the cover. Further, the instrument access port can be applied to the cover film after application of the film to a patient, and even after the dome is formed. This is shown, for example, in FIGS. 2D-F. FIG. 2D shows a dome formed by an inflated cover with an instrument access port held in proximity to the dome; FIG. 2E shows the instrument access port being applied to the dome; and FIG. 2F shows the instrument access port applied to the dome. The instrument access port can be provided with a lip which forms the access aperture in the film. Alternatively, an instrument that is passed through the instrument access port can pierce the cover to form the access aperture in the dome.

Figure 3A:
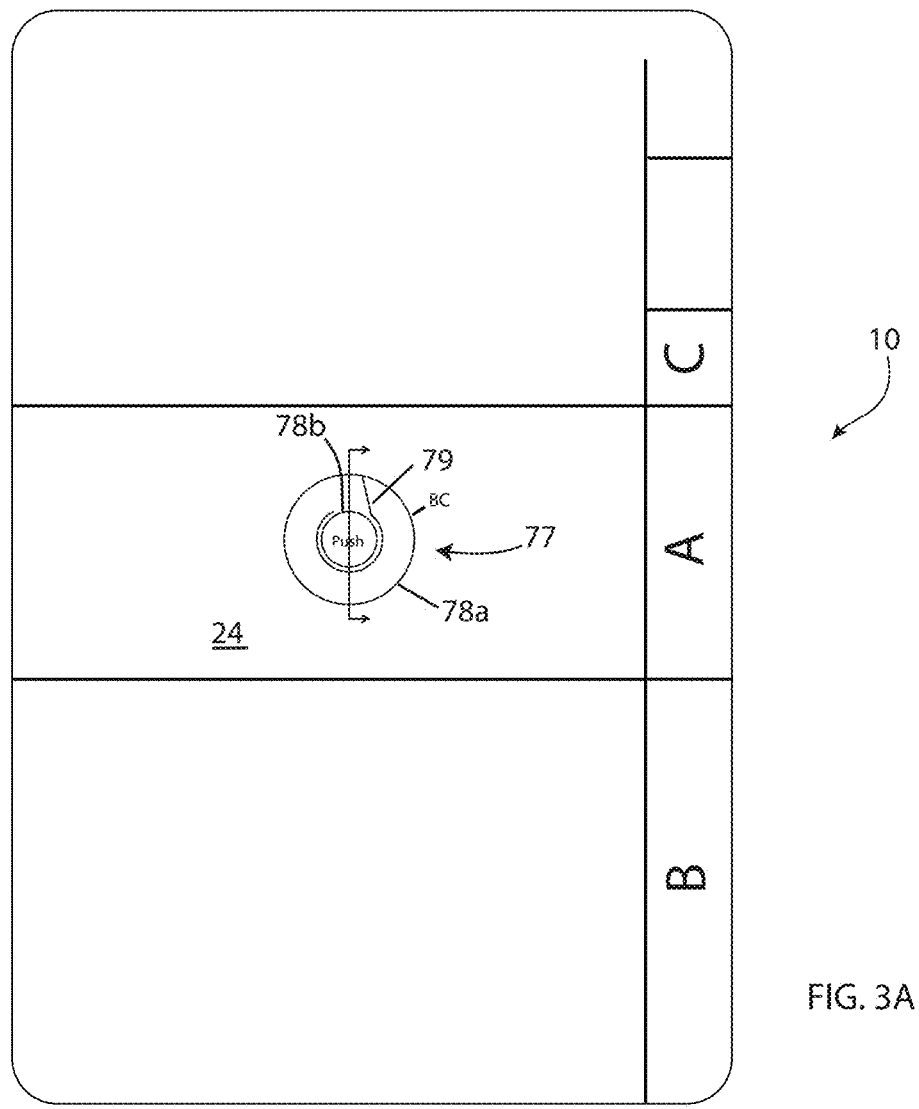
FIGS. 3A and 3B are plan and schematic cross-sectional views of the cover provided with the port assembly, but showing different cut lines to define the access opening to allow for optional mounting of the instrument access port to the cover.
Figure 3B:
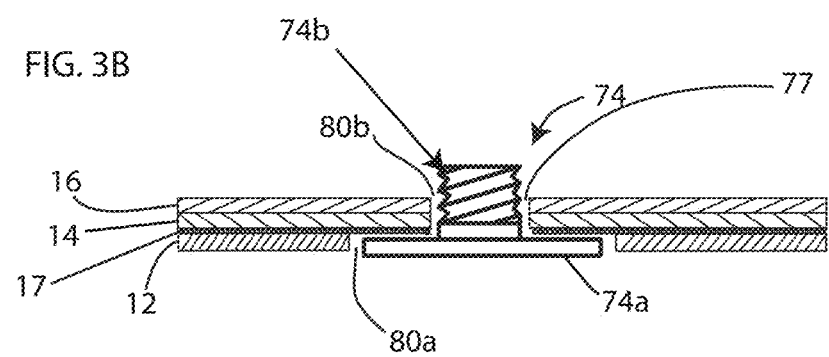

The cover in FIGS. 3A and 3B show another system which allows for the instrument access port to be applied to the cover by the surgical staff. In FIGS. 3A,B, the instrument access port 74 is applied to the bottom surface of the cover's stretchable ply 14. The dome-forming cover of FIGS. 3A,B is formed from a 3-ply film which is provided with an openable port assembly aperture 77 defined by an outer bottom cut 78a and an inner top-middle cut 78b that is concentric with the outer cut 78a. The outer bottom cut 78a is sized to form a hole 80a in the bottom ply 12 which will accept the base 74a of the port assembly 74. The inner, top-middle cut 78b is sized to form a hole 80b in the middle and top plies 14 and 16, respectively, which will admit the neck 74b of the port assembly 74 to pass therethrough. The top-middle cut 78b defines a "push tab" which when pressed, will separate the top and middle plies below the push tab, and the bottom ply, to form the holes 80a,b in the cover prior to removal of the bottom ply from the cover. As can be appreciated, the holes 80a,b define the port aperture 77. Opening the port aperture 77 will expose the adhesive of the middle ply 14 around the opening 80b, and the base 74a of the port assembly 74 can be pressed against the middle ply in the hole 80a to adhere the port assembly 74 in place on the cover 10. The cuts 78a,b are formed such that, if the port assembly is not going to be used, the respective plies will remain contiguous, that is, the bottom ply 12 surrounded by the cut 78a will be removed when the bottom ply/release liner is removed, and the top ply 16 surrounded by the cut 78b will be removed with the top ply. The cuts 78a,b could, for example, be perforated cuts, rather than continuous cuts. In addition, the cover includes a scythe-shaped cut 79, comprising a leg which extends from the outer cut 78a towards the inner cut 78b. This leg is not a radially extending cut, but rather defines an acute angle with a diameter of the two cuts. An arced cut then extends from the end of this leg, and substantially surrounds the inner cut 78b. The scythe-shaped cut 79 helps with the removal of the material to open the port assembly hole.

Figure 4A:
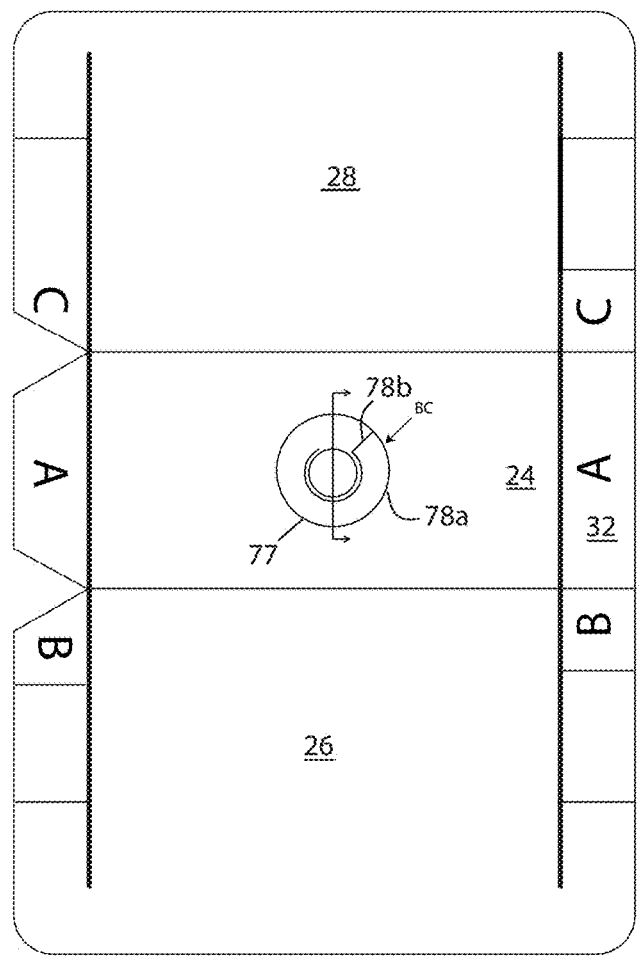
FIGS. 4A and 4B are plan and schematic cross-sectional views of a cover provided with a two-piece instrument access port assembly.
Figure 4B:
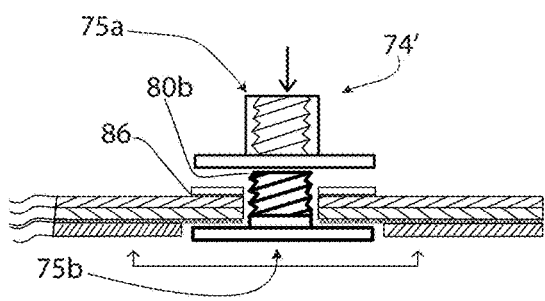
Figure 5:
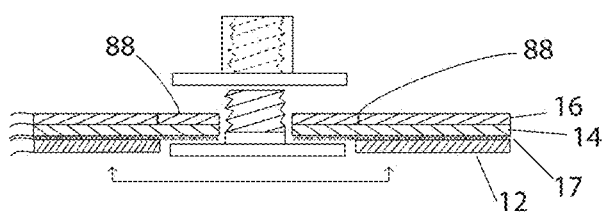
FIG. 5 is a schematic cross-sectional view of a cover provided with a two-piece instrument port assembly, but wherein the instrument access opening in the cover is formed slightly differently from the instrument access port in FIGS. 4A and 3A.

FIGS. 4A and 4B show a variation of the instrument access port assembly applied to a cover with an instrument port assembly aperture 77 in the cover which is defined by cuts 78a,b in the middle section 14. In this cover, an anti-friction washer 86 is provided around the port assembly aperture hole 80b to help reduce abrasions. The dome-forming cover is shown, in FIG. 4B, with an internally threaded instrument port assembly member 75a and externally threaded port assembly member 75b. The internally threaded member can be used in lieu of the externally threaded member. In this instance, the internally threaded member would define an instrument port assembly similar to FIG. 2C. Alternatively, the internally and externally threaded port members can be used together. In this instance, one port is threaded into (or onto) the other, such that the cover film(s) is(are) sandwiched between the bases of the two port assembly members. The port assembly can be fixed to the cover by any desired suitable connection method, i.e., twist lock, friction, quick connect, etc. Alternatively, the flange(s) of the port assembly member(s) can be heat sealed to the substrate.

Figure 6:
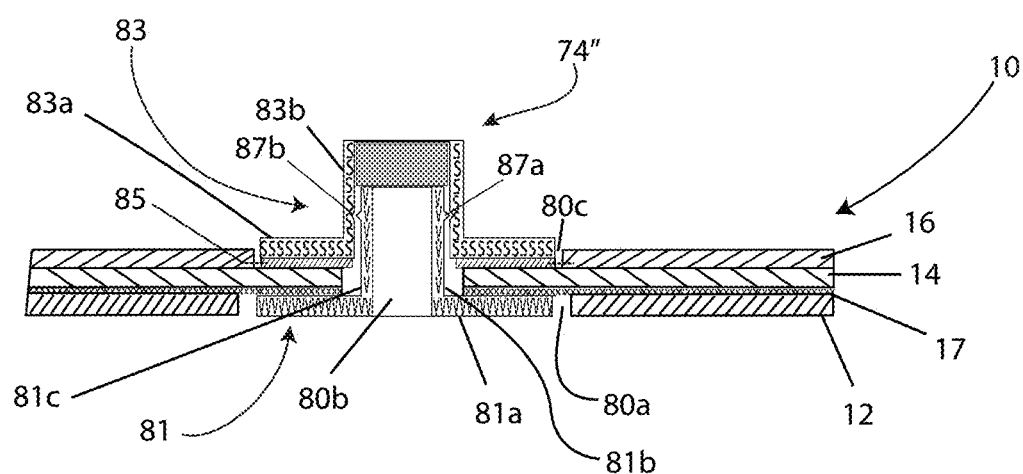
FIG. 6 is a schematic cross-sectional view of a snap-lock 2-part instrument port assembly.

FIG. 6 shows an instrument port assembly 74" comprising a male portion 81 and a female portion 83. The male portion 81 comprises a base 81a, a platform 81b, and a hollow stem 81c. The aperture 80a in the bottom ply 12 is sized to receive the base 81a, and the aperture 80b in the middle ply 14 is sized to receive the platform 81b. As can be appreciated, the base 81a of the male portion 81 will be adhered to the middle ply 14 by the adhesive layer 17. The female member 83 includes a base 83a and a hollow stem 83b. The base 83a of the female portion 83 can have a diameter sized generally equally to the base 81a of the male portion 81. The female portion stem 83b is sized to receive the male portion stem 81c. The aperture 80c in the top ply 16 is sized to receive the female portion base 83a. If desired, a double-sided adhesive film 85 can be applied to the bottom of the female portion base 83a to help adhere the female portion 83 to the middle ply 14. It is understood that a double-sided adhesive film is a film (or tape) with an adhesive applied to both surfaces (faces) of the film (tape). The port assembly 74" is further provided with a snap-lock to snappingly connect the male and female portions together. For example, the stem 81c of the male portion can be provided with an external annular rib 87a which is received in a circumferential groove 87b in the female portion stem 83b. If desired, the female portion could be provided with an interior rib, and the male portion could be provided with an external groove. The rib 87a and groove 87b are positioned on their respective stems such that the bases 81a and 83a of the male and female portions, respectively, will tightly sandwich the middle ply 14.

Figure 7:
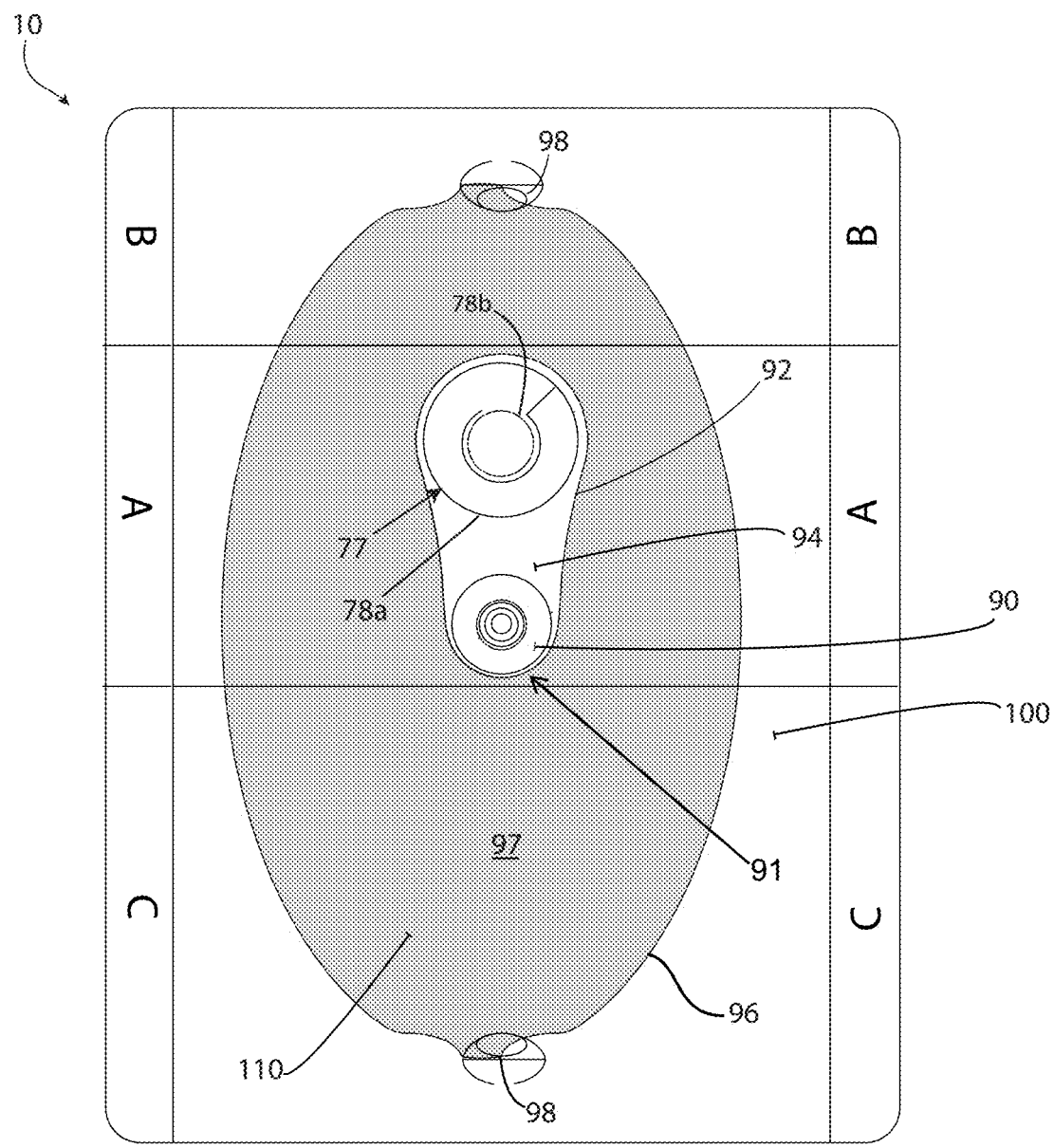
FIG. 7 is a plan view of a cover provided with an instrument access port and an inflation port.
Figure 9:
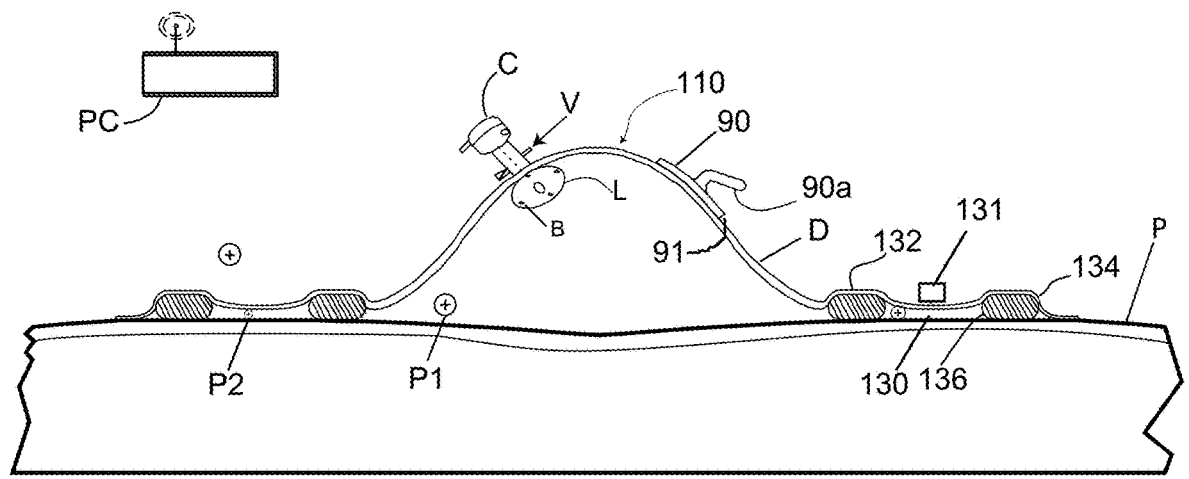
FIG. 9 is a cross-sectional view of a dome-forming cover defining an inner inflatable zone surrounded by a negative pressure zone.

FIG. 7 shows a cover 10 provided with an instrument access aperture 77 and an inflation port 90. Any of the instrument access ports of FIG. 2B, 3B, 4B, 5, or 6 can be positioned on the cover in alignment with the instrument access aperture. The inflation port is substantially similar to the inflation port disclosed and described in our PCT App. Pub No. WO 2016160997 entitled "Adhesive Therapeutic Cover", which is incorporated herein by reference, or as shown in FIG. 9 herein. The inflation port can be configured similarly to the instrument access port—that is, it can comprise a base that is secured to the cover and a stem, creating an air-tight seal or an air-lock 91 between the inflation zone and the external ambient environment when secured to the cover 10. However, rather than the stem being adapted to allow for passage of an instrument, the stem is adapted to be connected to a source of an inflating agent, such as a sterilized gas (i.e., $CO_2$, $N_2$, or air). The source of inflating agent can be remote from the cover (such as a pressurized tank or a building supply) which is connected to the inflation port by means of a hose. Alternatively, the inflation agent can be contained in a pressurized inflation cartridge which is connected to the inflation port. The inflation port 90 and the access port aperture 77 are surrounded by an inner top cut 92 such that the top ply 16 remains with the middle ply 14 in the immediate area surrounding the instrument access port and the inflation port. Thus, the top cut 92 defines port stabilization strip 94 surrounding the instrument access port and inflation port, which is shown to be generally pear-shaped. The top cut 92 closely surrounds the two ports, such that the ports effectively define opposite ends of the port stabilization strip. An outer top cut 96 surrounds the inner top cut 92 to define a removable section 97 of the top ply surrounded by a top ply frame 100. Thus, within the section 97, only the highly stretchable middle ply 14 remains. The outer top cut 96 is shown to be generally oval, but with flattened ends. Small tabs 98 are formed at the opposite ends of the top cut 96. The tabs 98 can be pulled to lift the removable section 97 of the top ply off the middle ply. As can be appreciated, the stabilization strip 94 is thicker than, and has a stretchability factor less than the stretchability factor of the surrounding area 97.

Once the cover has been applied to a patient, if desired, personnel can lift the removable section 97 of the top ply from the cover, to leave only the highly stretchable middle ply exposed. This forms an inflatable zone 110 of stretchable middle ply surrounding the less stretchable stabilization strip 94, and which is surrounded by the less stretchable top ply frame 100. The inflation port 90 can be connected to a source of pressurized, sterilized fluid and the zone 110 can be filled with the fluid. If the fluid is a gas (such as $CO_2$, $N_2$, air, etc.), the gas filled area can provide an enclosed dome through which procedures can be performed. On the other hand, if the fluid is a liquid or a gel, the fluid can be used to introduce medicament to the site. The frame 100 surrounding the inflatable zone 110 limits the area of the inflatable zone. The relatively non-stretchy top ply 16 in the frame 100 will substantially prevent the still covered middle ply in the frame 100 from stretching, and thus, the middle ply beneath the frame 100 will remain adhered to the patient. As can be appreciated, the size and shape of the dome generated by the inflatable zone can be altered by changing the size and shape of the frame 100.

Figure 8:
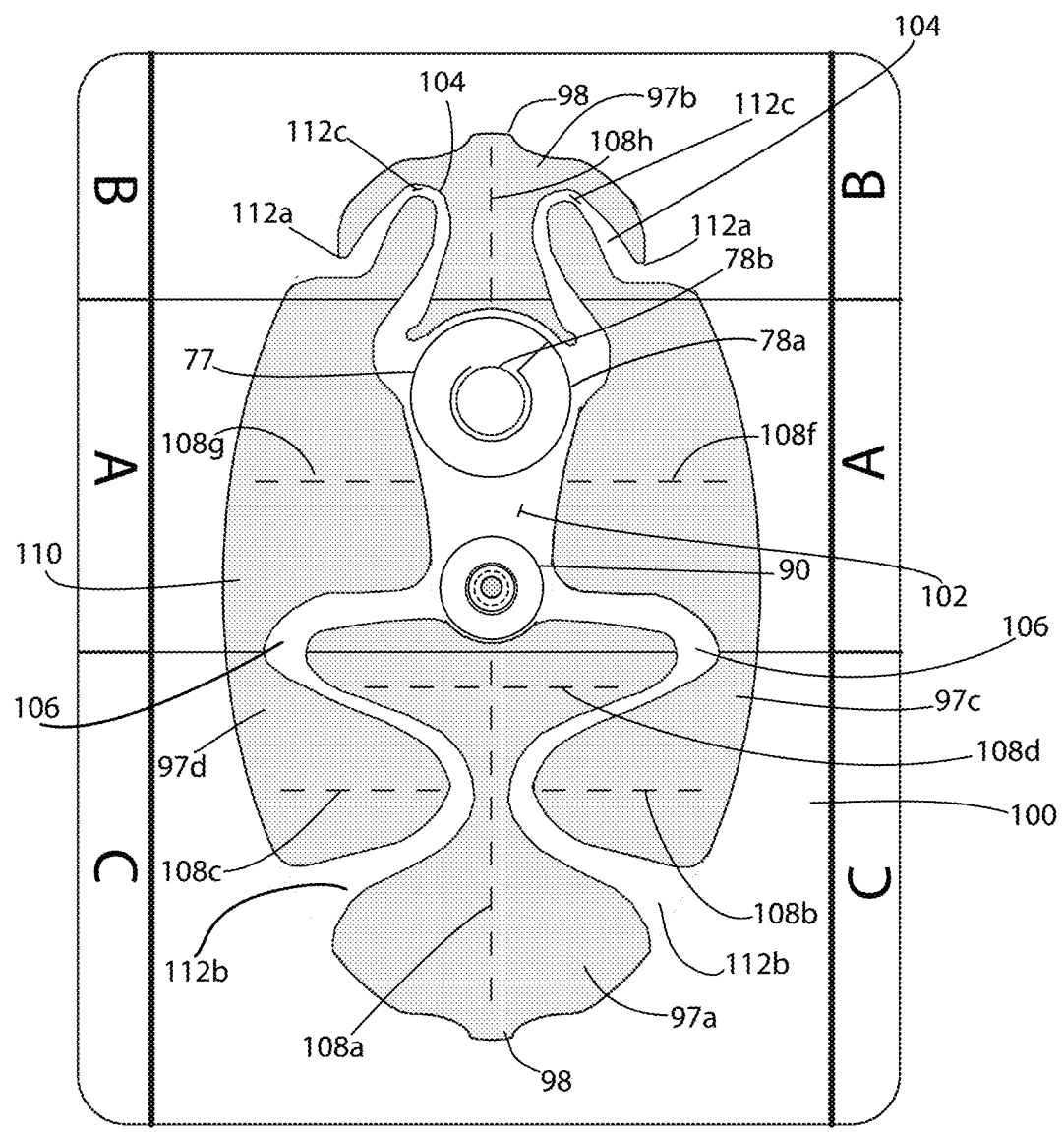
FIG. 8 is a plan view of a variation of the cover of FIG. 7.

FIG. 8 shows a cover provided with an inflation port and an access port aperture 77, and an alternatively shaped inflation zone and stabilization strip. A port stabilization strip 102 surrounds the inflation port and instrument access port aperture. Two upper, generally U-shaped arms 104 extend from the strip 102 adjacent the port assembly aperture 77. Additionally, two generally S-shaped legs 106 extend from the stabilization strip 102 proximate the inflation port 90. The arms 104 and legs 106 pass through the removable top ply section and connect to the frame 100 and define inflation limiting strips. As seen in the illustration, the stabilization strip 102 and the inflation limiting strips 104 and 106, in combination, give the impression of being generally frog-shaped. The inflation limiting strips 104 and 106, as noted, extend from the stabilization strip 102 to the frame 100 and thus divide the top ply removable section and the inflation zone 110 into top and bottom parts 97a,b and side parts 97c,d. The side parts 97c,d are identical to each other. Because of the difference in the shape of the inflation limiting strips (i.e., the arms 104 and legs 106), the top and bottom parts 97a,b are somewhat different from each other.

The tabs 98 are effective to remove the top and bottom parts 97a,b of the removable top ply section. However, because the top ply surrounding the inflation limiting strips separates the side sections from the end sections, removal of the end sections does not remove the side sections. To address this issue, the top ply removable section is provided with self-breakaway relief cuts 108a-h in the top ply. As a pressurized fluid (gas, gel, or liquid) is passed through the inflation port, the inflation zone 110 will begin to expand, and after a certain amount of stretching of the top ply, the release cuts 108a-h (which are preferably perforations) will break, allowing for unhindered inflation of the middle ply beneath the removable top ply sections 97a-d. The areas 112a-c, essentially at the ends of the arms (expansion limiting strips), and the ends of the feet (expansion limiting strips) of the removable top ply section 97b, and at the ends of the fingers extending from the top of the removable top ply sections 97*c,d*, respectively, form "hinge zones" In these hinge zones 112*a-d*, it is expected that the cover material is going to yield, i.e., expand at greater rates than the other areas. The hinge zones 112*a-d* have been designed so that the cross-sectional area of the stabilizing strip 102 and the inflation limiting strips 104 at the hinge zones 112*a-d* are sufficiently large to allow for the expected yielding, while still restricting inflation.

FIG. 9 shows, in schematic cross-section, an alternative cover defining an inflatable zone 110 (which can be substantially similar to the inflatable zone of the cover of either FIG. 7 or FIG. 8). Unlike the covers of FIGS. 7 and 8, the cover of FIG. 9 does not include a stabilization strip. In FIG. 9, the inflatable zone 110 is shown inflated to form a dome D. The film of the dome D can be only the middle ply 14, or both the middle ply 14 and top ply 16, of the cover film 10. That is, the dome D can be a one-ply dome or a two-ply dome. If desired, the dome D can be formed from a film of three or more plies. In this cover, the inflatable zone 110 is surrounded by a negative pressure zone 130. The negative pressure zone 130 can be separated from the inflatable zone 110 by adhesive 132 (such as two-sided tape) which will adhere the cover to the skin of a patient P and will form an air-tight seal between the inflatable zone 110 and the negative pressure zone 130, and will separate the two zones from each other. The adhesive 132 thus defines a frame or border surrounding the inflatable zone 110. The outer perimeter of the negative pressure zone 130 is defined by an area 134 of the cover which is adhered to the patient P in a manner that will create an air-tight seal between the inflatable zone and the exterior of the cover. Again, this outer border can be formed by 2-sided tape 136 which adheres the peripheral portion of the cover to the patient. The 2-sided tape used for the adhesive 132 or 136 can be, for example, two-sided tape available from 3M under the product codes 1567, 9776 or 9944, which contains a synthetic rubber adhesive. The negative pressure zone 130 is provided with a port (not shown) which can be connected to a vacuum source to reduce the pressure within the negative pressure zone 130. The port for the negative pressure zone can be similar to (or even identical to) the inflation port 90. Inasmuch as double-sided tape 132 and 136 is used to adhere the cover to the patient, the film which forms the cover can have a bottom surface that is otherwise free of adhesive. That is, the only adhesive on the cover is the adhesive of the tape borders 132 and 136.

To illustrate some of the flexibility of the dome forming cover, FIG. 9 shows an inflation (or insufflation) port 90 adhered to the outer surface of the dome D. The insufflation port 90 comprises a neck, stem, or connector 90*a* which can be connected to a source of a pressurized (preferably sterile) gas, as described above. A cannula C is mounted to the dome via an instrument access port, such as a port 74, 74', or 74". As is known, a variety of surgical instruments can be passed through the cannula C for use in a surgical procedure. The instrument access port can be provided with a seal to separate the interior of the dome from the ambient air external of the dome, creating an air-tight seal or an airlock 91. The seal can be incorporated into the access port. Alternatively, the access port can receive a surgical access device, such as is manufactured by Ethicon Endo-Surgery, Inc., and is disclosed in U.S. Pat. Nos. 8,137,267 and 9,427,255, which are incorporated herein by reference.

The instrument access port can be pre-positioned on the dome. However, with reference to FIGS. 2C and 6, an access port can be provided to enable a surgeon to position an access port anywhere on the dome. Further, as shown in FIGS. 2D-F, the instrument access port can be adhered to the cover after application of the cover to the patient (and even after inflation of the dome). A camera/light flange L can be positioned at the access port to providing lighting and/or camera capabilities within the dome. Such a camera could be an optical camera, or it could operate in other spectra, including UV, IR, etc., so that the surgical team can visualize other aspects of the operating site. As can be appreciated, with the camera positioned in the dome, the surgical staff can have a view of the surgical site that is not impeded by the material from which the cover is made. Further, the cover can be provided with bio-sensors B (shown associated with the camera/light flange). The bio-sensors can be used to monitor any of a number of parameters, including temperature, pressure, humidity, aseptic conditions, etc., within the dome D. As is known, aseptic conditions can be caused by microbes or *pseudomonas* within the dome. Sensors can also be provided to monitor conditions of the dome itself. For example, the strain or elongation of the dome-forming film can be monitored. An exhaust port or vent V can be provided. In FIG. 9, the vent V is shown as being incorporated in the instrument access port. If a vent is provided, the cover can include a sensor to analyze gas which exits through the vent. Further, the cover can be provided with pressure sensors P1 (in the dome) and P2 (in the negative pressure zone 130). The output of these pressure sensors will be transmitted to a controller PC, which can then monitor and control the pressure within the dome and the negative pressure zone.

Figure 10:
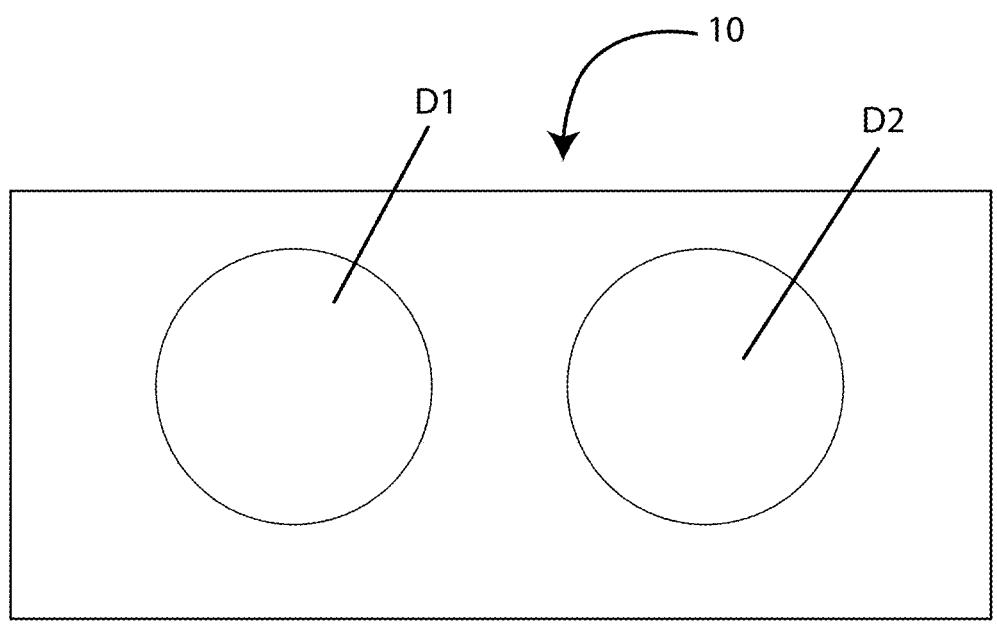
FIG. 10 is a schematic plan view of a cover with two discrete domed areas.

FIG. 9 shows a single dome D surrounded by a negative pressure zone. The cover of FIG. 9 is thus provided with an inflation port 90 in the dome and a vacuum port 131 in the negative pressure zone 130. If desired, the cover can be provided with two or more positive pressure zones (i.e., two or more domed areas). FIG. 10 shows a cover 10 with two domed areas D1 and D2. The two domed areas will each have their own inflation ports, such that each dome can be inflated separately. Additionally, each dome can be provided with its own pressure sensor, such that the pressure within the domes can be controlled separately. Because the cover is adhesively applied to the patient, the sizes of the domes are controlled by the pressure within each of the domes. For certain procedures, it may be desirable to maintain the two domes separate from each other. However, in other procedures, it may be desirable to join the two domes. To do so, the pressure in one (or both) domes is increased until the domes merge. The direction of growth of the domes can be controlled, for example, by providing a frame or border around the domes. Such a frame can be formed from double-sided tape, as in FIG. 9, or by removing one or more plies of film in the respective inflation zones for the domes, to thereby leave a multi-ply film forming the borders for the domes, such as in FIGS. 7 and 8. Alternatively, the direction of growth of the domes can be controlled by manually directing the growth of the dome by pressing against the patient to ensure that the one dome expands toward the other dome. As can be appreciated, the borders for the domes can be formed, and the domes can be inflated, in such a manner as to assure that the domes do not merge.

Figure 11:
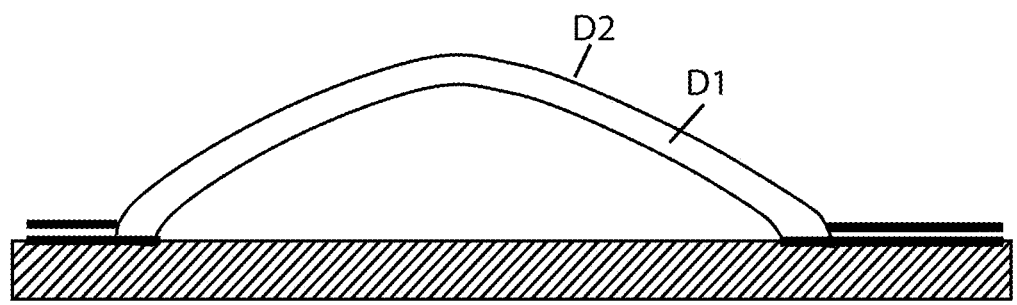
FIG. 11 is a schematic cross-sectional view of a cover defining a dome within a dome.

In other situations, it may be desirable to have a dome within a dome. FIG. 11 schematically shows such a situation. In this instance, the stretchability of a multi-ply cover is relied upon to form a first inner dome D1 and a second outer dome D2. As can be appreciated, the outer dome has a perimeter that is at least the size of the inner dome's perimeter. In this instance, a single inflation port with multiple outlets can be used, as long as the outlets are not in communication with each other. Preferably, the separate inflation port would be constructed such that the outlets can be individually opened and closed, to provide independent control of the inflation of the two domes. Alternatively, separate inflation ports can be provided for each of the two domes.

Figure 12:
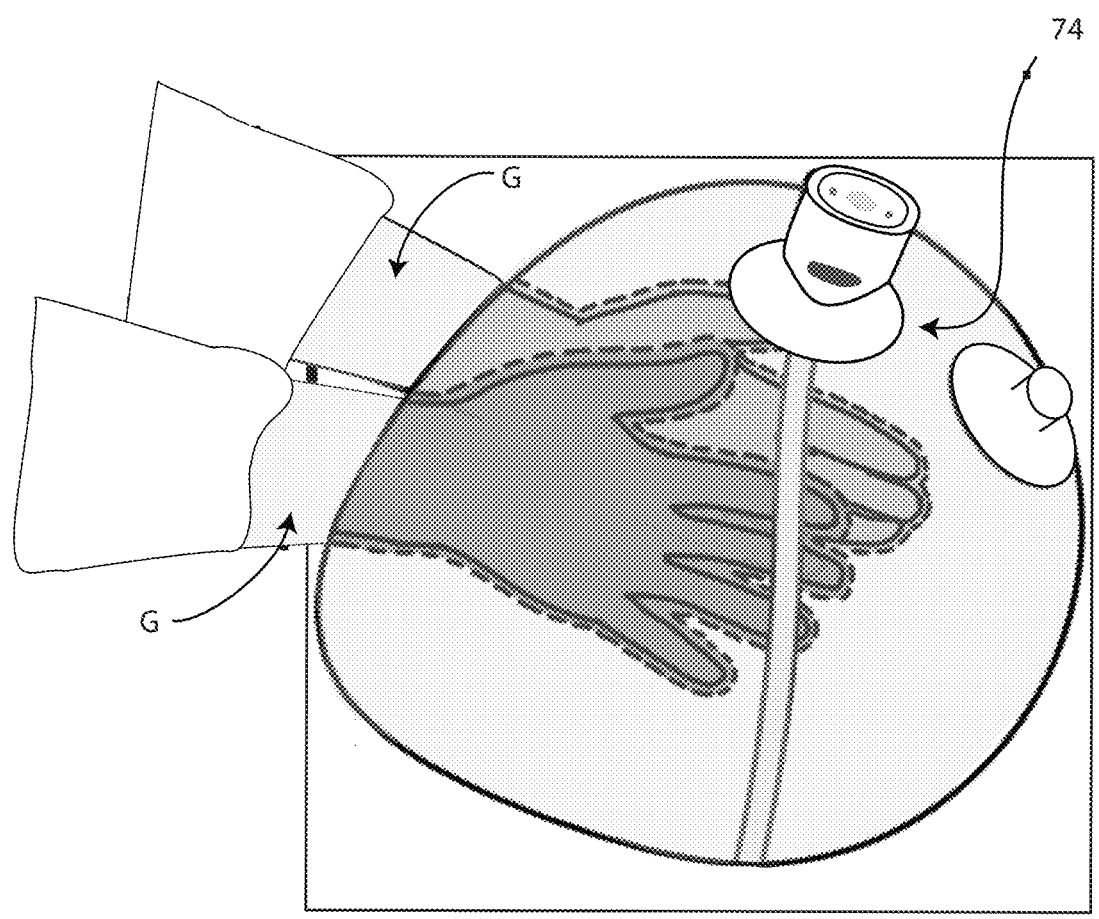
FIG. 12 is a perspective view of a dome-forming cover with attached gloves to enable manual manipulation of tissue and instruments under the dome.
Figure 13:
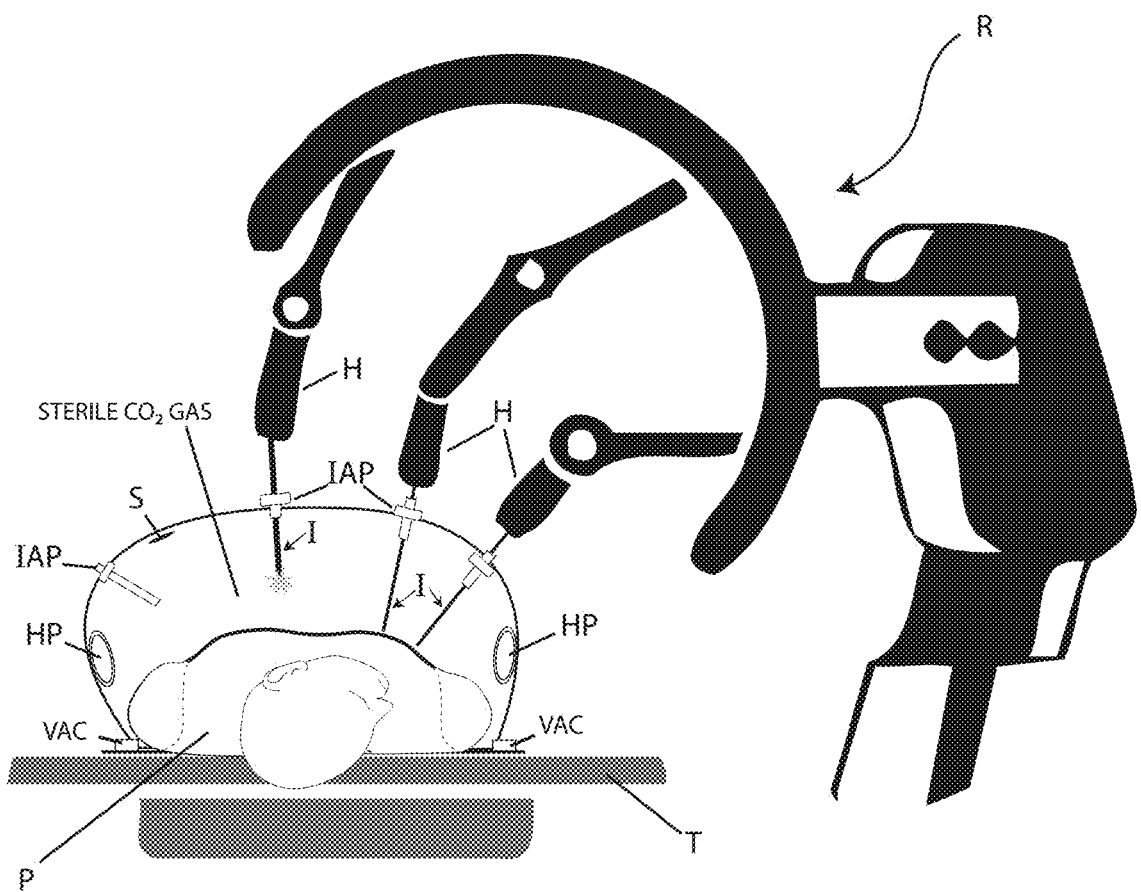
FIG. 13 is a schematic view of a dome-forming cover applied across a patient with surgical instruments connected to a robot.

FIGS. 12 and 13 show dome-forming covers with hand ports. In FIG. 12, the cover is provided with gloves G to allow for manual manipulation of instruments or tissue under the dome or within the surgical site. The gloves G include a hand portion which receives the wearer's hand and a sleeve portion extending from the hand portion. The sleeve is connected to the cover at a free end of the sleeve. The connection of the sleeve to the cover is such that, when the glove is external of the dome, the interior of the glove is exposed. Thus, when a user places his or her hand in the glove, the users hand will enter the dome within his/her hand in the glove, and the exterior of the glove exposed within the dome.

In FIG. 13, the cover is provided with hand ports HP through which a gloved hand can pass. Unlike the cover of FIG. 12, gloves are not pre-connected to the cover. Rather, the hand ports HP can be iris ports which comprise a closable (iris) aperture which can be enlarged to allow a gloved hand to pass through the hand port. It will be appreciated that when a gloved hand is passed through the hand port HP, there will not be an air/gas tight seal around the wearer's hand and or arm. However, as long as the flow of air/gas into the dome exceeds the flow of air/gas exiting the dome through the hand port, the dome will remain inflated. FIG. 13 also shows a sensor S secured to the inner surface of the dome film. The sensor S is a temperature sensor, but could be any desired type of sensor. For example, the sensor could be a gas or humidity sensor to sense the gas concentration or the humidity within the dome. If desired, multiple sensors could be included within the dome. Additionally, FIG. 13 shows a robot R having robot hands H which hold, and are capable of manipulating, instruments I which extend through instrument access ports (IAP) in the dome.

The cover of FIG. 13 varies from the covers of FIGS. 7-9. In the covers of FIGS. 7-9, the covers were applied only to the patient. That is, the totality of the cover is applied to the patient, and the area under the dome is fully on the patient body. However, in FIG. 13, the lateral or side edges of the cover are secured to the table T on opposite sides of the patient P. The cover can be secured to the table T by means of adhesive on the underside of the cover film, adhesive tape, or a vacuum seal. The top and bottom edges of the cover extend across the patient (for example, across the top and bottom of the patient's torso or abdomen). As can be appreciated, there may be an opening into the dome at the point where the cover transitions from the table to the patient. However, by keeping this opening as small as possible, the positive pressure within the dome will maintain the dome inflated as long as the flow of gas into the dome exceeds the flow of gas exiting the dome through the opening.

Figure 14A:
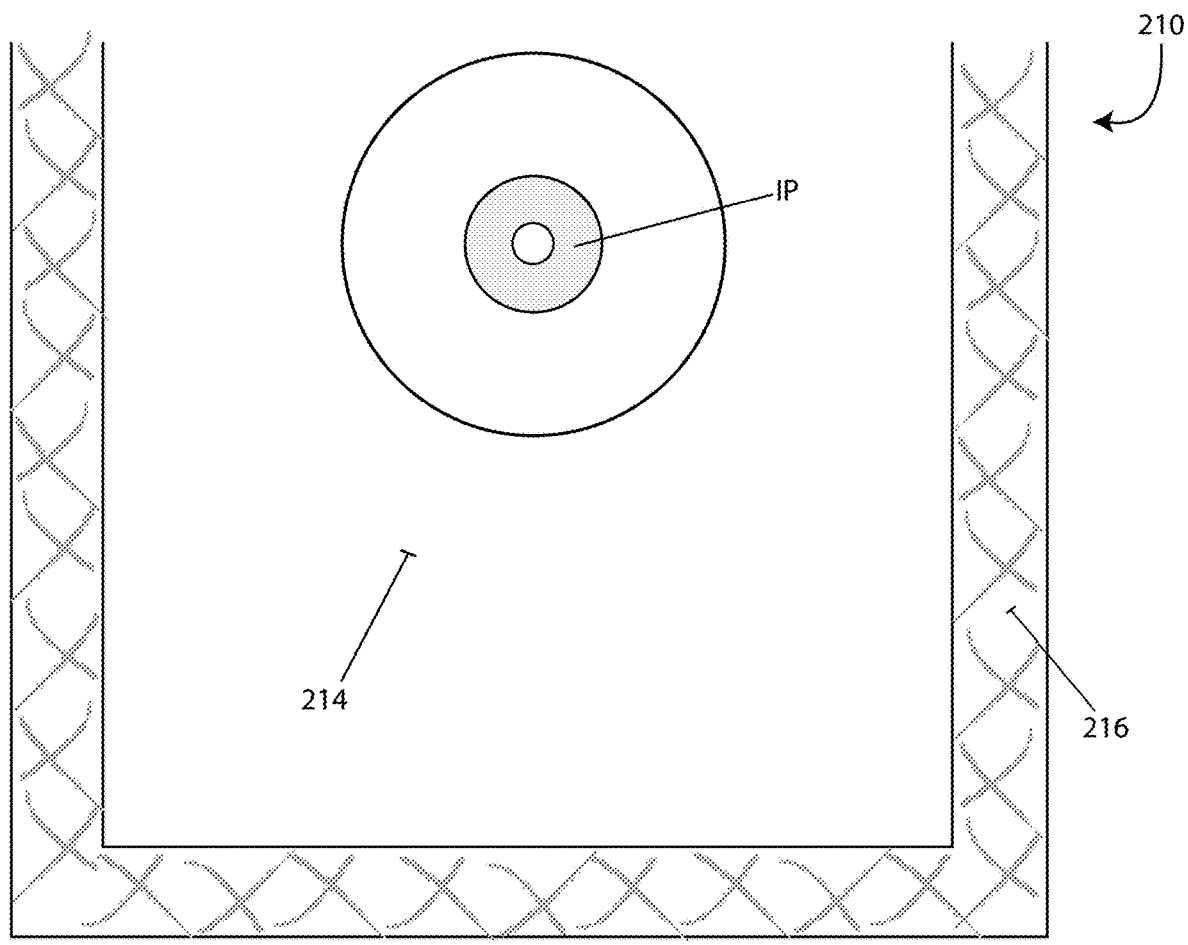
FIGS. 14A-14C are fragmentary plan (FIG. 14A) and cross-sectional views (FIG. 14B-C), of a dome-forming cover comprised of an antimicrobial incisable drape which is adhered to a patient and a dome-forming stretchable ply secured to the incisable drape.

FIGS. 14A,B show a further alternative to the dome-forming cover. The cover 210 in FIG. 14 comprises an incisable, antimicrobial film 212 which is adhered to a patient by means of adhesive. A release liner 213 on the bottom surface of the antimicrobial film 212 protects the adhesive of the film 212. A preferred film from which the antimicrobial film and its release liner are made is IOBAN® available from 3M. A dome-forming film 214 is adhered to the antimicrobial film 212 about the periphery of the two films, to define a border 216. The border 216 can be formed by a heat seal or by an adhesive which secures or bonds the dome-forming film 214 to the antimicrobial film 212. The bottom surface of the dome-forming film 214 inside of the border 216 is free of adhesive, such that the dome-forming film 214 is adhered to the antimicrobial film 212 only at the border 216. The dome-forming film can be a single-ply or multi-ply film, as may be desired. Preferably, the dome-forming film is made from a material similar to the material from which the middle ply 14 of the cover film 10 (FIG. 1A) is made. Additionally, the dome-forming film can include UV filtering properties or can be composted of a material having UV filtration properties. For example, the dome-forming film can be formed from a polyurethane or polyethylene material with elongation rate up to about 500%. An inflation port IP is provided which is aligned with an opening 218 in the dome-forming film 214. The inflation port IP is adapted to be connected to a source of a pressurized gas to allow for inflation of the dome-forming film 214, and can be identical to the inflation port 90 of FIG. 7 or 8. Although not shown in FIGS. 14A,B, the cover 210 can be provided with instrument access ports.

Figure 14B:
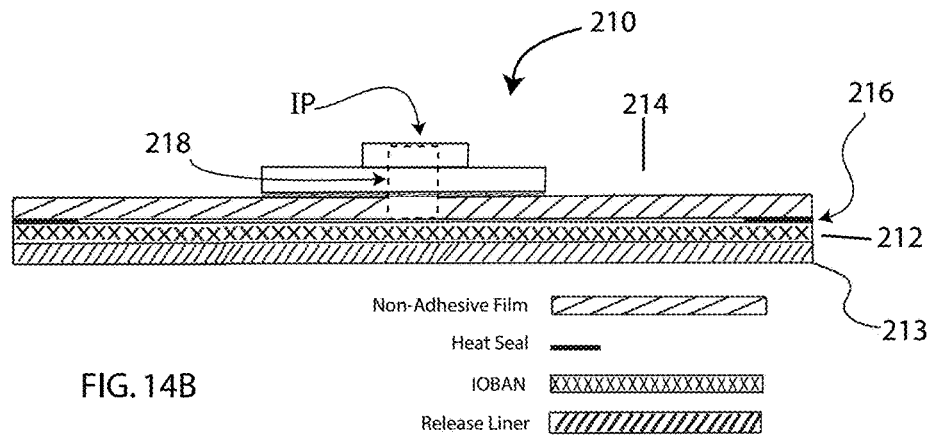
Figure 14C:
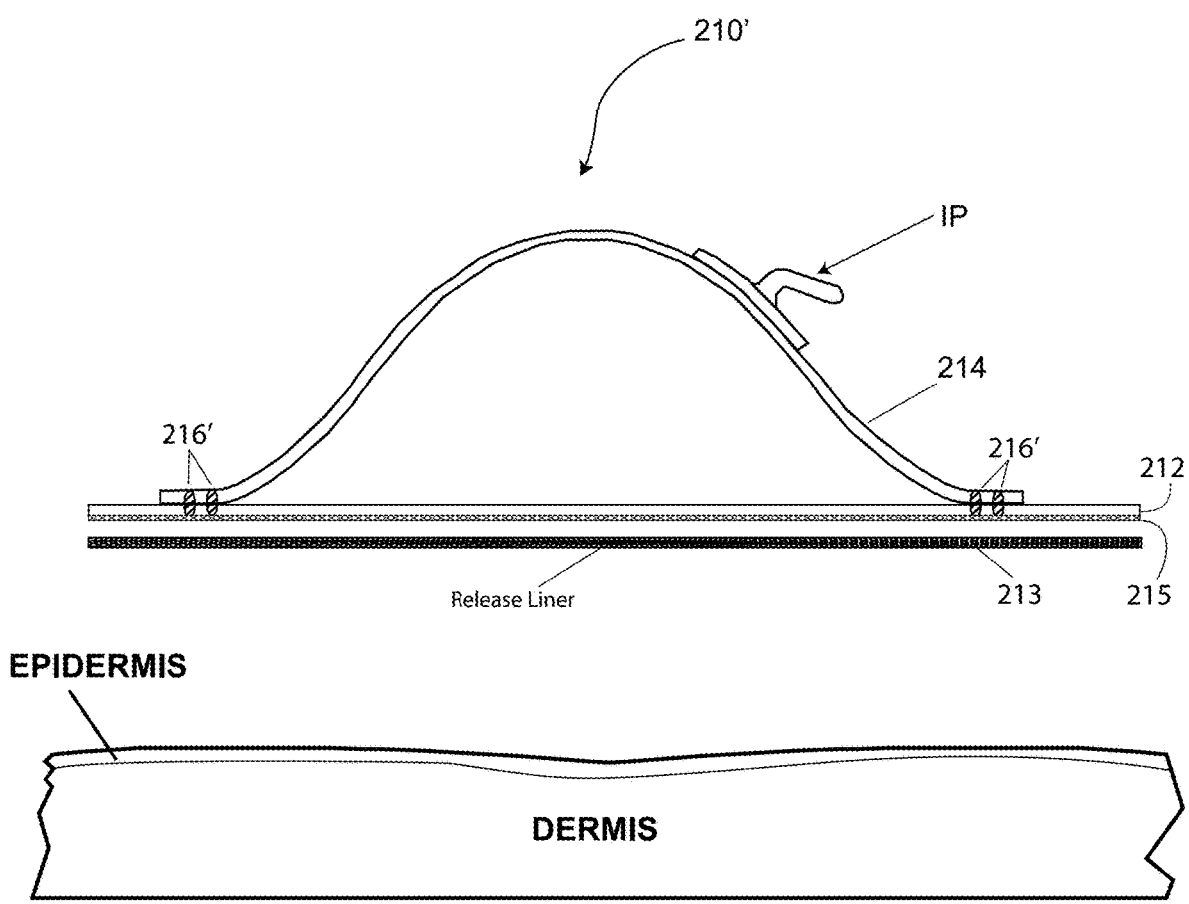

In FIG. 14C, a cover 210' is shown which is substantially similar to the cover 210 of FIGS. 14A,B. In FIG. 14C, the cover 210' is shown in an inflated dome-forming condition and with the release liner 213 separated from the antimicrobial film 212 to expose the adhesive layer 215. The cover 210' differs from the cover 210, in that whereas the cover 210 had a single seal defining the border of the inflatable zone, the cover 210' has a double seal (and preferable a double heat seal) 216'. The border forming seal 216 of the cover 210 is thicker (or wider) than the individual seals of the double seal 216' of the cover 210'.

Instrument access ports, when used with a cover, such as an IOBAN antimicrobial drape, which is adhered to the patient over substantially the entire surface area of the cover, allow for the cover/drape to be used during minimally invasive surgical procedures, including laparoscopic procedures. However, the provision of a domed protected area, as shown in FIGS. 7-9, and 14C around the incision can create a substantially sterile zone around an incision site, even in an open surgery. It is anticipated that the ability to form a dome under which a procedure can be conducted and the atmosphere of which can be controlled will help reduce SS's (surgical site infections), which currently cost the medical community millions/billions of dollars annually. One way to control the frequency of an SSI is to not expose the incision/wound to ambient atmospheres in the operating room (OR). The provision of a dome over the surgical site allows for control of temperature, humidity, types of gas, pressure, and atmosphere at the surgical site, all while never exposing the open incision to ambient atmosphere. As can be appreciated, this is beneficial, not only in operating rooms, but in battlefield treatment zones, field hospitals where there is limited or no electricity, etc.

The covers disclosed herein can be used in conjunction with surgeries which are either partially or completely robotic, surgeries (either open or laparoscopic) in which a surgeon handles the surgical instruments directly, or in surgeries wherein the surgeon controls the surgical instruments remotely. Procedurally, a surgical procedure using one of the covers disclosed above could be carried out as follows:

1. The patient is prepped using a sterile solution.
2. An anti-microbial drape, such as an IOBAN® drape, available from 3M, is preferably applied to the patient as an initial barrier to protect against microbial flora and fauna that remain on the skin layer despite the prep.

3. The dome-forming cover is applied to the patient with its stretchable dome-forming ply having an elongation factor sufficient to enable the dome-forming ply to be expanded, insufflated, or inflated to form a dome of sufficient size to allow for instrumentation above the anticipated incision site. If a cover, such as the cover 210 or 210' of FIGS. 14A-C is used wherein the dome forming ply is sealed or otherwise pre-fixed to the anti-microbial film, these steps (2) and (3) can be carried out simultaneously. Depending on the procedure, the cover can define a single dome, multiple spaced-apart domes, or domes within domes. Additionally, the cover can include gloves and/or hand ports, prepositioned instrument access ports, and/or sensors positioned in the inflatable zone of the dome-forming ply of the cover.

4. A source of sterile, pressurized gas (fluid) is attached to the inflation port of the cover via a hose, for example, and the inflating gas is introduced into the inflatable zone under pressure to form a dome or plenum over the surgical site of a desired diameter, to define an enclosed sterile volume over the surgical site. For example, the gas can be introduced at a pressure of 10-20 milibars (gage).

5. Instruments are passed through instrument access ports. The instrument access ports preferably have valves allowing for passage of instrumentation through the dome, and limit the amount of gas that will exit the dome through the instrument access port. The instrument access ports can be manufactured into the cover or secured to the dome after adhering the cover to the patient or after inflation of the dome. A surgeon (or robotic surgical device, in the case of a robotic procedure) may utilize the ports and provide light, camera, magnification, and/or instrumentation to manipulate tissue and provide traction and counter traction. Larger ports (such as glove ports) lateral to the operating room table can be provided which are large enough to accommodate a surgeon's gloved hands to allow for manual manipulation intra-dome.

In the three (or more) ply cover of FIG. 1A, the adhesive layer 17 is formed between the release liner 12 and the middle ply 14. The adhesive layer can cover substantially the entire bottom surface of the middle ply, such that the middle ply, prior to inflation and formation of the dome, will be adhered to the patient over substantially the entire middle ply. Alternatively, the adhesive can be applied to selected areas of the middle ply to define an inner portion of the middle ply that is free of adhesive and which is surrounded by adhesive. This adhesive-free area will thus define the inflation zone for the carrier, and the surrounding portions of the middle ply to which adhesive is applied will define a frame which helps define the shape of the base of the dome. The dome, as can be appreciated, can be circular or oval. However, the periphery of the dome can be polygonal as well. For example, the dome can be rectangular at its periphery.

As can be appreciated, the ability to provide a cover having a stretchable ply which is operatively adhered to a patient over an incision site and which can be stretched or inflated to form a dome about the incision site will even further isolate the surgical site from ambient atmosphere. This can help to reduce surgical site infections. In a traditional hospital operating room, the use of the dome to further isolate the incision site from the ambient operatory air can reduce operating room costs related to gowning methods, and can reduce the need for operating room lights and other traditional operating room equipment and methodology. By using a cover comprising a stretchable, inflatable ply, a domed free space or plenum is provided under which robotic and/or manual instrumentation can be carried out to perform surgical procedures. The environment under the dome can be completely controlled. Most importantly, the positive pressure under the dome is substantially sterile.

As various changes could be made in the above constructions without departing from the scope of the invention, it is intended that all matter contained in the above description or shown in the accompanying drawings shall be interpreted as illustrative and not in a limiting sense. For example, the frame surrounding the inflation zone can be formed by the adhesive which adheres the ply 14 to the patient. In this instance, the cover 10 could be formed from a 2-ply film (i.e., a film having only a release liner and the stretchable dome-forming ply). These variations are merely illustrative.

The invention claimed is:

1. A medical cover comprising at least one stretchable ply adapted to be adhered, at least in part, to a patient during use of the medical cover; said medical cover defining top and bottom edges and first and second side edges; said at least one stretchable ply being substantially co-extensive with the top and bottom edges and first and second side edges of said medical cover; said medical cover comprising:
    an inflatable zone defined by at least a first portion of said at least one stretchable ply; said inflatable zone having a zone edge which is spaced from the top and bottom edges and the first and second side edges of said medical cover, and
    at least one inflation port in said inflatable zone; said at least one inflation port being connectable to a source of a fluid or gas; the at least one stretchable ply in the inflatable zone stretching and expanding when said fluid or gas is injected into said inflatable zone to define a pressurized enclosed area having a sterile atmosphere;
    a frame portion defined by at least a second portion of said at least one stretchable ply which surrounds said inflatable zone, said frame portion having adhesive on a lower surface thereof whereby said medical cover is adapted to be adhesively adhered at least in part to the patient, said at least one stretchable ply of said inflatable zone stretching to define a dome upon introduction of said fluid or gas beneath said at least one stretchable ply of said inflatable zone, said dome defining a free space between the patient and the at least one stretchable ply of the inflatable zone; and
    at least one instrument access port mounted to the at least one stretchable ply of the inflation zone and through which a surgical instrument can be introduced into the dome during a procedure;
    wherein said at least one instrument access port is preassembled to the at least one stretchable ply of the inflation zone or can be added to the at least one stretchable ply of inflation zone after inflation of the dome; and
    wherein said at least one stretchable ply is made from an incisable material such that adding said at least one instrument access port to the at least one stretchable ply will not compromise the sterility of the pressurized enclosed area under the dome.

2. The medical cover of claim 1 further comprising a first film having an upper surface and a lower surface; said at least one stretchable ply being secured to said lower surface of said first film; said first film comprising an adhesive layer on said lower surface of said first film.

3. The medical cover of claim 2 wherein said frame surrounding said inflatable zone is defined by a junction of said inflatable zone with said first film.

4. The medical cover of claim 2 wherein said first film is an antimicrobial film.

5. The medical cover of claim 2 wherein said at least one stretchable ply is secured to said first film by adhesive, heat sealing, or double-sided adhesive tape.

6. The medical cover of claim 1 wherein said at least one stretchable ply has an adhesive applied to at least a portion of a bottom surface of said at least one stretchable ply; whereby said at least one stretchable ply is adapted to be adhered directly to a patient during use.

7. The medical cover of claim 6, wherein said at least one stretchable ply comprises an adhesive-free zone surrounded by said adhesive.

8. The medical cover of claim 6 further including a release liner which is removable to expose said adhesive.

9. The medical cover of claim 1 further including a top ply above said at least one stretchable ply; said at least one stretchable ply having a stretchability factor greater than a stretchability factor of the top ply.

10. The medical cover of claim 1 wherein said at least one inflation port comprises a plurality of said inflation ports; each of said inflation portion ports independently inflating a dome; whereby discrete domes can be formed in said medical cover.

11. The medical cover of claim 1 wherein when said at least one stretchable ply is inflated, the dome can support ports, trocars, cannulas and other instruments/devices which may be desired to be introduced into the interior of the dome through the at least one instrument access port.

12. The medical cover of claim 1 further including an air-lock port; said air-lock port defining a sealed area that is attached to the inflated dome; wherein the air-lock port is adapted to exchange atmosphere from external of the dome to internal of the dome or vice versa.

13. The medical cover of claim 1 wherein said at least one stretchable ply has UV filtering properties.

14. The medical cover of claim 1 wherein said medical cover includes a ply of UV filtering material adjacent said at least one stretchable ply.

15. The medical cover of claim 1 including one or more monitoring devices to monitor desired parameters within said dome; said one or more monitoring devices including one or more of the following:
- a sensor for analyzing gas exiting through an exhaust port of said medical cover;
- at least one pressure sensor and a controller; said sensor being positioned to be in said dome upon inflation of said inflatable zone; said pressure sensor emitting a signal indicative of the pressure within the dome; said controller receiving said signal from said at least one sensor to control the source of fluid or gas in response to the sensed pressure within the dome to maintain a desired pressure within the dome;
- an ink (or reactive agent) which changes color in response to a change in the atmosphere within dome;
- at least one sensor which can detect conditions of the atmosphere within the dome;
- an optical sensor attached to, or gatherable to, said at least one stretchable ply; said optical sensor being adapted to obtain images of the surgical site within said dome;
- a controller to control a temperature within the dome to warm or cool the patient as needed.

16. The medical cover of claim 1 wherein said at least one stretchable ply is curable under exposure to light, heat, or other reaction, to become rigid.

17. The medical cover of claim 1 wherein said at least one stretchable ply is radiopaque.

18. A medical cover comprising at least one stretchable ply adapted to be adhered, at least in part, to a patient during use of the medical cover; said medical cover defining top and bottom edges and first and second side edges; said medical cover comprising:
- an inflatable zone defined by at least a portion of said at least one stretchable ply,
- at least one inflation port in said inflatable zone; said inflation port being connectable to a source of a fluid or gas;
- a frame surrounding said inflatable zone, said at least one stretchable ply of said inflatable zone stretching to defining a dome upon introduction of said fluid or gas beneath said at least one stretchable ply of said inflatable zone, said dome defining a free space between the patient and the at least one stretchable ply of the inflatable zone; and
- at least one instrument access port mounted to the at least one stretchable ply of the inflation zone and through which a surgical instrument can be introduced into the dome during a procedure;
- said at least one instrument access port comprising an instrument access port member; said instrument access port member comprising a base which is adhered to said at least one stretchable ply and a hollow neck which extends from said base; and wherein said medical cover includes a top ply above said at least one stretchable ply and a release liner to which said at least one stretchable ply is removably adhered; whereby said at least one stretchable ply defines a middle ply of said medical cover; said at least one instrument access port being defined by an outer bottom cut in said release liner and an inner top-middle cut surrounded by said outer bottom cut, said outer bottom cut defining a hole in said release liner sized to receive the base of said instrument access port member, and said inner top-middle cut defining a hole extending through said top and middle plies sized to allow passage of said hollow neck therethrough, whereby said instrument access port defines an instrument access aperture when the material inside of said outer bottom cut and inner top-middle cut from said medical cover is removed.

19. The medical cover of claim 18 wherein said top ply is formed from a stretchable film, said inflatable zone is further defined by at least a portion of said top ply, said top ply being at least as stretchable as said at least one stretchable ply; said at least one inflation port being adapted to separately stretch and inflate said at least one stretchable ply and said top ply; whereby, when said medical cover is inflated, said top ply defines an outer dome surrounding said dome.

20. A medical cover comprising at least one stretchable ply adapted to be adhered, at least in part, to a patient during use of the medical cover; said medical cover defining top and bottom edges and first and second side edges; said at least one stretchable ply being substantially co-extensive with the edges of said medical cover; said medical cover comprising:
- an inflatable zone defined by at least a first portion of said at least one stretchable ply; said inflatable zone having a zone edge which is spaced from the top, bottom, and side edges of said medical cover, and at least one inflation port in said inflatable zone; said at least one inflation port being connectable to a source of a fluid or gas; the at least one stretchable ply in the inflatable zone stretching and expanding when said fluid or gas is injected into said inflatable zone to define a pressurized enclosed area having a sterile atmosphere;

a frame portion defined by at least a second portion of said at least one stretchable ply which is adapted to be adhesively adhered to the patient, said frame portion surrounding said inflatable zone, said at least one stretchable ply of said inflatable zone stretching to define a dome upon introduction of said fluid or gas beneath said at least one stretchable ply of said inflatable zone, said dome defining a free space between the patient and the at least one stretchable ply of the inflatable zone, said frame limiting the area of the dome;

at least one instrument access port mounted to the at least one stretchable ply of the inflation zone and through which a surgical instrument can be introduced into the dome during a procedure; and a hand port adapted to enable a practitioner to introduce his/her hand into the free space.

21. A medical cover comprising at least one stretchable ply adapted to be adhered, at least in part, to a patient during use of the medical cover; said medical cover defining top and bottom edges and first and second side edges; said at least one stretchable ply being substantially co-extensive with the edges of said medical cover; said medical cover comprising:

an inflatable zone defined by at least a first portion of said at least one stretchable ply; said inflatable zone having a zone edge which is spaced from the top and bottom edges and the first and second side edges of said medical cover, and at least one inflation port in said inflatable zone; said at least one inflation port being connectable to a source of a fluid or gas; the at least one stretchable ply in the inflatable zone stretching and expanding when said fluid or gas in injected into said inflatable zone to define a pressurized enclosed area having a sterile atmosphere;

a frame portion defined by at least a second portion of said at least one stretchable ply which is adapted to be adhesively adhered to the patient, said frame portion surrounding said inflatable zone, said at least one stretchable ply of said inflatable zone stretching to define a dome upon introduction of said fluid or gas beneath said at least one stretchable ply of said inflatable zone, said dome defining a free space between the patient and the at least one stretchable ply of the inflatable zone; and at least one instrument access port mounted to the at least one stretchable ply of the inflation zone and through which a surgical instrument can be introduced into the dome during a procedure; and at least one glove adhered to said at least one stretchable ply of the inflatable zone; said at least one glove comprising a hand portion adapted to receive a wearer's hand and a sleeve portion extending from the hand portion; the sleeve portion being connected to the at least one stretchable ply at a free end of the sleeve portion at an opening in the medical cover; the connection of the sleeve portion to the at least one stretchable ply being such that, in use when the glove is external of the dome, the interior of the glove is exposed, such that when a user places his or her hand in the glove, the user's hand will enter the dome through the opening in the at least one stretchable ply with his/her hand in the glove, and the exterior of the glove exposed within the dome.

22. A method of forming a sterile substantially enclosed zone about a surgical site on a patient, the method comprising:

adhering a medical cover at least in part to the patient to cover the surgical site;
the medical cover comprising at least one stretchable ply, a first portion of which defines an inflatable zone configured to expand when inflated to maintain a pressurized sterile atmosphere surrounding the surgical site; said inflatable zone, when inflated, defining a dome said inflatable zone having a zone edge which is spaced from edges of said medical cover; said inflatable zone being surrounded by an inflation limiting frame portion defined at least in part by at least a second portion of said at least one stretchable ply, at least a portion of said second portion of said at least one stretchable ply being adapted to be adhesively adhered to the patient when in use, said medical cover further comprising an inflation port in the inflatable zone; the inflation port being adapted to be connected to a source of sterile gas;

said medical cover further comprising at least one hand port adapted to enable a practitioner to introduce his/her hand into a volume defined by the dome; and introducing the sterile gas under pressure beneath the at least one stretchable ply of the inflatable zone to stretch said at least one stretchable ply of said inflatable zone and thereby form an inflated dome over the surgical site.

23. A medical cover comprising at least one stretchable ply adapted to be adhered, at least in part, to a patient during use of the medical cover; said medical cover defining top and bottom edges and first and second side edges; said medical cover comprising:

an inflatable zone defined by at least a portion of said at least one stretchable ply, at least one inflation port in said inflatable zone; said inflation port being connectable to a source of a fluid or gas;

a frame surrounding said inflatable zone, said at least one stretchable ply of said inflatable zone stretching to defining a dome upon introduction of said fluid or gas beneath said at least one stretchable ply of said inflatable zone, said dome defining a free space between the patient and the at least one stretchable ply of the inflatable zone;

at least one instrument access port mounted to the at least one stretchable ply of the inflation zone and through which a surgical instrument can be introduced into the dome during a procedure; and a ring surrounding said dome and a vacuum port in communication with said ring; whereby, a zone of negative pressure can be formed around said dome.

24. A medical cover comprising at least one stretchable ply adapted to be adhered, at least in part, to a patient during use of the medical cover; said medical cover defining top and bottom edges and first and second side edges; said at least one stretchable ply being substantially co-extensive with the top and bottom edges and first and second side edges of said medical cover; said medical cover comprising:

an inflatable zone defined by at least a first portion of said at least one stretchable ply; said inflatable zone having a zone edge which is spaced from the top and bottom edges and first and second side edges of said medical cover, and at least one inflation port in said inflatable zone; said at least one inflation port being connectable to a source of a fluid or gas; the at least one stretchable ply in the inflatable zone stretching and expanding when said fluid or gas in injected into said inflatable zone to define a pressurized enclosed area having a sterile atmosphere;

a frame portion defined by at least a second portion of said at least one stretchable ply which is adapted to be adhesively adhered to the patient, said frame portion surrounding said inflatable zone, said at least one stretchable ply of said inflatable zone stretching to define a dome upon introduction of said fluid or gas beneath said at least one stretchable ply of said inflatable zone, said dome defining a free space between the patient and the at least one stretchable ply of the inflatable zone; and at least one instrument access port mounted to the at least one stretchable ply of the inflation zone and through which a surgical instrument can be introduced into the dome during a procedure; wherein the inflated dome can support said surgical instrument; and wherein said surgical instrument can be added to or removed from the at least one instrument access port without compromising the sterile atmosphere of the pressurized enclosed area of said inflatable zone.

25. A method of forming a sterile substantially enclosed zone about a surgical site on a patient; the method comprising:

adhering a medical cover at least in part to the patient to cover the surgical site; the medical cover comprising at least one stretchable ply, a first portion of which defines an inflatable zone configured to expand when inflated to maintain a pressurized sterile atmosphere surrounding the surgical site, said inflatable zone having a zone edge which is spaced from edges of said medical cover; said inflatable zone being surrounded by an inflation limiting frame portion defined at least in part by at least a second portion of said at least one stretchable ply, at least a portion of said second portion of said at least one stretchable ply being adapted to be adhesively adhered to the patient when in use, said medical cover further comprising an inflation port in the inflatable zone; the inflation port being adapted to be connected to a source of sterile gas;

introducing the sterile gas under pressure beneath the at least one stretchable ply of the inflatable zone to stretch said at least one stretchable ply of said inflatable zone and thereby form an inflated dome defining a covered area over the surgical site; and securing an instrument access port to the inflated dome without compromising the integrity of the covered area; said instrument access port being adapted to permit surgical devices to be passed into the dome.

26. The method of claim 25 wherein the method comprises manipulating an atmospheric pressure within the dome to provide a desired clinical effect.

27. The method of claim 25 wherein an area enclosed by the dome defines a free space sufficiently large to accommodate robotic arms/instrumentation while maintaining an aseptic environment within the dome.

28. The method of claim 25 wherein the method comprises controlling a temperature within the dome to warm or cool the patient as needed.

29. A medical cover comprising at least one stretchable ply adapted to be adhered, at least in part, to a patient during use of the medical cover; said medical cover defining top and bottom edges and first and second side edges; said at least one stretchable ply being substantially co-extensive with the top and bottom edges and the first and second side edges of said medical cover; said medical cover comprising:

an inflatable zone defined by at least a first portion of said at least one stretchable ply; said inflatable zone having a zone edge which is spaced from the top and bottom edges and the first and second side edges of said medical cover, and at least one inflation port in said inflatable zone; said at least one inflation port being connectable to a source of a fluid or gas; the at least one stretchable ply in the inflatable zone stretching and expanding when said fluid or gas in injected into said inflatable zone to define a pressurized enclosed area having a sterile atmosphere;

a frame portion defined by at least a second portion of said at least one stretchable ply which is adapted to be adhesively adhered to the patient, said frame portion surrounding said inflatable zone, said at least one stretchable ply of said inflatable zone stretching to define a dome upon introduction of said fluid or gas beneath said at least one stretchable ply of said inflatable zone, said dome defining a free space between the patient and the at least one stretchable ply of the inflatable zone; and at least one instrument access port mounted to the at least one stretchable ply of the inflation zone and through which a surgical instrument can be introduced into the dome during a procedure, wherein said surgical instrument comprises a magnification instrument, said magnification instrument being configured to capture and project images from said procedure onto a screen external to the inflatable zone of said medical cover.

30. The medical cover as claimed in claim 29, wherein said surgical instrument is a laparoscopic telescope.

31. A method of forming a sterile substantially enclosed zone about a surgical site on a patient, the method comprising:

adhering a medical cover at least in part to the patient to cover the surgical site; the medical cover comprising at least one stretchable ply, a first portion of which defines an inflatable zone configured to expand when inflated to maintain a pressurized sterile atmosphere surrounding the surgical site, said inflatable zone having a zone edge which is spaced from edges of said medical cover; said inflatable zone being surrounded by an inflation limiting frame portion defined at least in part by at least a second portion of said at least one stretchable ply, at least a portion of said second portion of said at least one stretchable ply being adapted to be adhesively adhered to the patient when in use, said medical cover further comprising an inflation port in the inflatable zone; the inflation port being adapted to be connected to a source of sterile gas; and, introducing the sterile gas under pressure beneath the at least one stretchable ply of the inflatable zone to stretch said at least one stretchable ply of said inflatable zone and thereby form an inflated dome over the surgical site;

wherein the adhering step further comprises adhering side portions of the medical cover to a table on which the patient is placed.

* * * * *

UNITED STATES PATENT AND TRADEMARK OFFICE
CERTIFICATE OF CORRECTION

PATENT NO. : 11,246,674 B1  
APPLICATION NO. : 15/787673  
DATED : February 15, 2022  
INVENTOR(S) : Galbierz et al.

Page 1 of 1

It is certified that error appears in the above-identified patent and that said Letters Patent is hereby corrected as shown below:

In the Specification

Column 1, Line 32, replace "SS's" with "SSI's"  
Column 1, Line 59, replace "SS's" with "SSI's"  
Column 14, Line 45, replace "SS's" with "SSI's"

In the Claims

Claim 15 - Column 17, Line 60, replace "dome" with "said dome"  
Claim 15 - Column 17, Line 63, replace "gatherable" with "adherable"

Signed and Sealed this  
Twelfth Day of July, 2022

Katherine Kelly Vidal  
*Director of the United States Patent and Trademark Office*